(12) United States Patent
Kangawa et al.

(10) Patent No.: US 10,653,637 B2
(45) Date of Patent: May 19, 2020

(54) PREVENTIVES OR REMEDIES FOR HEPATOPATHY

(75) Inventors: Kenji Kangawa, Osaka (JP); Hiroshi Hosoda, Chiba (JP)

(73) Assignee: Kenji Kangawa, Osaka (JP)

( * ) Notice: Subject to any disclaimer, the term of this patent is extended or adjusted under 35 U.S.C. 154(b) by 1674 days.

(21) Appl. No.: 10/554,875

(22) PCT Filed: Apr. 30, 2004

(86) PCT No.: PCT/JP2004/006365
§ 371 (c)(1),
(2), (4) Date: Sep. 19, 2006

(87) PCT Pub. No.: WO2004/096260
PCT Pub. Date: Nov. 11, 2004

(65) Prior Publication Data
US 2007/0219114 A1    Sep. 20, 2007

(30) Foreign Application Priority Data

Apr. 30, 2003 (JP) .................................. 2003-126088

(51) Int. Cl.
*A61K 31/00* (2006.01)
*A61K 38/25* (2006.01)

(52) U.S. Cl.
CPC .............. *A61K 31/00* (2013.01); *A61K 38/25* (2013.01)

(58) Field of Classification Search
None
See application file for complete search history.

(56) References Cited

U.S. PATENT DOCUMENTS

| 5,492,891 | A * | 2/1996 | Skakkeb et al. ................. 514/12 |
| 6,967,237 | B2 | 11/2005 | Bednarek |
| 7,385,026 | B1 * | 6/2008 | Kangawa et al. ............ 530/324 |
| 2001/0020012 | A1 * | 9/2001 | Andersen et al. ............... 514/46 |
| 2003/0096411 | A1 * | 5/2003 | Michalopoulos ... A61L 27/3804 435/373 |

FOREIGN PATENT DOCUMENTS

| CA | 2 380 058 A1 | 2/2001 |
| EP | 1197496 A1 | 4/2002 |
| JP | 2004-00251 A | 1/2004 |
| WO | WO 01/07475 A1 | 1/2001 |
| WO | WO 01/56592 | 8/2001 |
| WO | WO 2001/056592 A1 | 8/2001 |
| WO | WO 2001/92292 | 12/2001 |
| WO | WO 02/060472 | 8/2002 |

OTHER PUBLICATIONS

Matsumoto et al., "Structure-Activity Relationship of Ghrelin: Pharmacological Study of Ghrelin Peptides," Biomedical and Biophysical Research Communications, (2001), vol. 287, pp. 142-146.*
Wonke B, "New approaches to the management of hepatitis and endocrine disorders in Cooley's anemia," Ann N Y Acad Sci. Jun. 30, 1998;850:232-41.*
Broglio F, et al., "Ghrelin: much more than a natural growth hormone secretagogue," Isr Med Assoc J. Aug. 2002;4(8):607-13.*
Murata et al., "Ghrelin Modulates the Downstream Molecules in Insulin Signaling in Hepatoma Cells," The Journal of Biological Chemistry, (2002), vol. 277, No. 7, pp. 5667-5674.
Tacke et al., "Ghrelin in Chronic Liver Disease," Journal of Hepatology, (2003), vol. 38, pp. 447-454.
Tacke et al. "Ghrelin is a Parameter of Catabolism in Patients with Chronic Liver Disease," Hepatology, (2002), vol. 36, No. 4, Part 2, p. 530A.
Supplementary European Search Report of Sep. 3, 2009 for EPO Application No. EP 04 73 0725.
Assy, et al. (1997) Journal of Hepatology 27: 796-802.
Donaghy, et al. (1997) Gastroenterology 113: 1617-1622.
Wallace, et al. (2002) The Journal of Clinical Endocrinology & Metabolism 87(6): 2751-2759.
European Office Action in European Application No. 04 730 725.1, dated Oct. 13, 2010.

* cited by examiner

*Primary Examiner* — Thomas S Heard
(74) *Attorney, Agent, or Firm* — Hunton Andrews Kurth LLP

(57) ABSTRACT

The present invention relates to a preventive or a therapeutic agent for hepatopathy, comprising, as an effective ingredient, a polypeptide derivative having an activity of binding to growth hormone secretagogue receptor and thus elevating intracellular calcium ion concentration, and having one amino acid sequence selected from the group consisting of amino acid sequences represented by SEQ ID NOS: 1 to 22, or an amino acid sequence in which one to several amino acids are deleted, substituted or added at the amino acid residues other that the first to forth amino acid residues from the amino-terminus in the said amino acid sequence, or a pharmacologically acceptable salt thereof. The preventive or the therapeutic agent for hepatopathy in accordance with the present invention is useful as a drug suitable for treating or preventing hepatic diseases such as hepatitis, liver cirrhosis and hepatic insufficiency. Further, the preventive or the therapeutic agent for hepatopathy in accordance with the present invention is also useful as an agent of promoting hepatic regeneration and hepatic function recovery after hepatectomy.

10 Claims, 3 Drawing Sheets

Specification includes a Sequence Listing.

A

B

SEQUENCE LISTING

```
<160> NUMBER OF SEQ ID NOS: 69

<210> SEQ ID NO 1
<211> LENGTH: 28
<212> TYPE: PRT
<213> ORGANISM: Homo Sapiens
<220> FEATURE:
<221> NAME/KEY: MOD_RES
<222> LOCATION: (3)..(3)
<223> OTHER INFORMATION: Acylation with acetic acid, butyric acid,
      valeric acid, octanoic acid or decanoic acid
<220> FEATURE:
<221> NAME/KEY: MISC_FEATURE
<223> OTHER INFORMATION: Amino acid sequence for human endogenous
      peptides of growth hormone secretagogue

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with acetic acid, butyric acid,
      valeric acid, octanoic acid or decanoic acid
<220> FEATURE:
<221> NAME/KEY: MISC_FEATURE
<223> OTHER INFORMATION: Amino acid sequence for human endogenous
      peptides (27 amino acids) of growth hormone secretagogue

<400> SEQUENCE: 2

Gly Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 3
<211> LENGTH: 28
<212> TYPE: PRT
<213> ORGANISM: Rattus norvegicus
```

```
<220> FEATURE:
<221> NAME/KEY: MOD_RES
<222> LOCATION: (3)..(3)
<223> OTHER INFORMATION: Acylation with acetic acid, butyric acid,
      valeric acid, octanoic acid or decanoic acid
<220> FEATURE:
<221> NAME/KEY: MISC_FEATURE
<223> OTHER INFORMATION: Amino acid sequence for rat endogenous peptides
      of growth hormone secretagogue

<400> SEQUENCE: 3

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 27
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Acylation with acetic acid, butyric acid,
      valeric acid, octanoic acid or decanoic acid
<220> FEATURE:
<221> NAME/KEY: MISC_FEATURE
<223> OTHER INFORMATION: Amino acid sequence for rat endogenous peptides
      (27 amino acids) of growth hormone secretagogue

<400> SEQUENCE: 4

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 5
<211> LENGTH: 28
<212> TYPE: PRT
<213> ORGANISM: Mus musculus
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for mouse endogenous
      peptides of growth hormone secretagogue

<400> SEQUENCE: 5

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Sus scrofa (pig)
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for porcine endogenous
      peptides of growth hormone secretagogue

<400> SEQUENCE: 6
```

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 7
<211> LENGTH: 27
<212> TYPE: PRT
<213> ORGANISM: Sus scrofa (pig)
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for porcine endogenous
      peptides (27 amino acids) of growth hormone secretagogue

<400> SEQUENCE: 7

Gly Ser Ser Phe Leu Ser Pro Glu His Gln Lys Val Gln Arg Lys Glu
1               5                   10                  15

Ser Lys Lys Pro Ala Ala Lys Leu Lys Pro Arg
            20                  25

<210> SEQ ID NO 8
<211> LENGTH: 27
<212> TYPE: PRT
<213> ORGANISM: Bos taurus
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for bovine endogenous
      peptides (27 amino acids) of growth hormone secretagogue

<400> SEQUENCE: 8

Gly Ser Ser Phe Leu Ser Pro Glu His Gln Lys Leu Gln Arg Lys Glu
1               5                   10                  15

Ala Lys Lys Pro Ser Gly Arg Leu Lys Pro Arg
            20                  25

<210> SEQ ID NO 9
<211> LENGTH: 27
<212> TYPE: PRT
<213> ORGANISM: Ovis aries
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for ovine endogenous
      peptides (27 amino acids) of growth hormone secretagogue

<400> SEQUENCE: 9

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 10
<211> LENGTH: 28
<212> TYPE: PRT
<213> ORGANISM: Canis familiaris
<220> FEATURE:
<221> NAME/KEY: MOD_RES

```
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for dog endogenous peptides
      of growth hormone secretagogue

<400> SEQUENCE: 10

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 11
<211> LENGTH: 21
<212> TYPE: PRT
<213> ORGANISM: Anguilla japonica
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for eel endogenous peptides
      of growth hormone secretagogue
<220> FEATURE:
<221> NAME/KEY: MOD_RES
<222> LOCATION: (11)..(11)
<223> OTHER INFORMATION: AMIDATION

<400> SEQUENCE: 11

Gly Ser Ser Phe Leu Ser Pro Ser Gln Arg Pro Gln Gly Lys Asp Lys
1               5                   10                  15

Lys Pro Pro Arg Val
            20

<210> SEQ ID NO 12
<211> LENGTH: 23
<212> TYPE: PRT
<213> ORGANISM: Oncorhynchus mykiss
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MOD_RES
<222> LOCATION: (23)..(23)
<223> OTHER INFORMATION: AMIDATION
<220> FEATURE:
<221> NAME/KEY: MISC_FEATURE
<223> OTHER INFORMATION: Amino acid sequence for rainbow trout
      endogenous peptides (23 amino acids) of growth hormone
      secretagogue

<400> SEQUENCE: 12

Gly Ser Ser Phe Leu Ser Pro Ser Gln Lys Pro Gln Val Arg Gln Gly
1               5                   10                  15

Lys Gly Lys Pro Pro Arg Val
            20

<210> SEQ ID NO 13
<211> LENGTH: 20
<212> TYPE: PRT
<213> ORGANISM: Oncorhynchus mykiss
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MOD_RES
```

```
<222> LOCATION: (20)..(20)
<223> OTHER INFORMATION: AMIDATION
<220> FEATURE:
<221> NAME/KEY: MISC_FEATURE
<223> OTHER INFORMATION: Amino acid sequence for rainbow trout
      endogenous peptides (20 amino acids) of growth hormone
      secretagogue

<400> SEQUENCE: 13

Gly Ser Ser Phe Leu Ser Pro Ser Gln Lys Pro Gln Gly Lys Gly Lys
1               5                   10                  15

Pro Pro Arg Val
            20

<210> SEQ ID NO 14
<211> LENGTH: 24
<212> TYPE: PRT
<213> ORGANISM: Gallus domesticus
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for chicken endogenous
      peptides of growth hormone secretagogue

<400> SEQUENCE: 14

Gly Ser Ser Phe Leu Ser Pro Thr Tyr Lys Asn Ile Gln Gln Gln Lys
1               5                   10                  15

Gly Thr Arg Lys Pro Thr Ala Arg
            20

<210> SEQ ID NO 15
<211> LENGTH: 24
<212> TYPE: PRT
<213> ORGANISM: Gallus domesticus
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for chicken endogenous
      peptides of growth hormone secretagogue

<400> SEQUENCE: 15

Gly Ser Ser Phe Leu Ser Pro Thr Tyr Lys Asn Ile Gln Gln Gln Lys
1               5                   10                  15

Asp Thr Arg Lys Pro Thr Ala Arg
            20

<210> SEQ ID NO 16
<211> LENGTH: 26
<212> TYPE: PRT
<213> ORGANISM: Gallus domesticus
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for chicken endogenous
      peptides of growth hormone secretagogue

<400> SEQUENCE: 16

Gly Ser Ser Phe Leu Ser Pro Thr Tyr Lys Asn Ile Gln Gln Gln Lys
1               5                   10                  15
```

Asp Thr Arg Lys Pro Thr Ala Arg Leu His
            20                  25

<210> SEQ ID NO 17
<211> LENGTH: 27
<212> TYPE: PRT
<213> ORGANISM: Rana cafesbeiana
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for frog endogenous
      peptides of growth hormone secretagogue

<400> SEQUENCE: 17

Gly Leu Thr Phe Leu Ser Pro Ala Asp Met Gln Lys Ile Ala Glu Arg
1               5                   10                  15

Gln Ser Gln Asn Lys Leu Arg His Gly Asn Met
            20                  25

<210> SEQ ID NO 18
<211> LENGTH: 28
<212> TYPE: PRT
<213> ORGANISM: Rana cafesbeiana
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for frog endogenous
      peptides of growth hormone secretagogue

<400> SEQUENCE: 18

Gly Leu Thr Phe Leu Ser Pro Ala Asp Met Gln Lys Ile Ala Glu Arg
1               5                   10                  15

Gln Ser Gln Asn Lys Leu Arg His Gly Asn Met Asn
            20                  25

<210> SEQ ID NO 19
<211> LENGTH: 20
<212> TYPE: PRT
<213> ORGANISM: Tilapia nilotica
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MOD_RES
<222> LOCATION: (20)..(20)
<223> OTHER INFORMATION: AMIDATION
<220> FEATURE:
<221> NAME/KEY: MISC_FEATURE
<223> OTHER INFORMATION: Amino acid sequence for tilapia endogenous
      peptides of growth hormone secretagogue

<400> SEQUENCE: 19

Gly Ser Ser Phe Leu Ser Pro Ser Gln Lys Pro Gln Asn Lys Val Lys
1               5                   10                  15

Ser Ser Arg Ile
            20

<210> SEQ ID NO 20
<211> LENGTH: 22
<212> TYPE: PRT
<213> ORGANISM: Silurus asotus
<220> FEATURE:

```
<221> NAME/KEY: MOD_RES
<222> LOCATION: (22)..(22)
<223> OTHER INFORMATION: AMIDATION
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for catfish endogenous
      peptides of growth hormone secretagogue

<400> SEQUENCE: 20

Gly Ser Ser Phe Leu Ser Pro Thr Gln Lys Pro Gln Asn Arg Gly Asp
1               5                   10                  15

Arg Lys Pro Pro Arg Val
            20

<210> SEQ ID NO 21
<211> LENGTH: 23
<212> TYPE: PRT
<213> ORGANISM: Silurus asotus
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for catfish endogenous
      peptides of growth hormone secretagogue

<400> SEQUENCE: 21

Gly Ser Ser Phe Leu Ser Pro Thr Gln Lys Pro Gln Asn Arg Gly Asp
1               5                   10                  15

Arg Lys Pro Pro Arg Val Gly
            20

<210> SEQ ID NO 22
<211> LENGTH: 28
<212> TYPE: PRT
<213> ORGANISM: Equus caballus
<220> FEATURE:
<221> NAME/KEY: MOD_RES
<222> LOCATION: (3)..(3)
<223> OTHER INFORMATION: Acylation with octanoic acid or decanoic acid
<220> FEATURE:
<221> NAME/KEY: MISC_FEATURE
<223> OTHER INFORMATION: Amino acid sequence for equine endogenous
      peptides of growth hormone secretagogue

<400> SEQUENCE: 22

Gly Ser Ser Phe Leu Ser Pro Glu His His Lys Val Gln His Arg Lys
1               5                   10                  15

Glu Ser Lys Lys Pro Pro Ala Lys Leu Lys Pro Arg
            20                  25

<210> SEQ ID NO 23
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (9)..(9)
<223> OTHER INFORMATION: AMIDATION

<400> SEQUENCE: 23
```

-continued

```
Gly Ser Ser Phe Leu Ser Pro Glu His
1               5
```

<210> SEQ ID NO 24
<211> LENGTH: 28
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Acylation with acetic acid

<400> SEQUENCE: 24

```
Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25
```

<210> SEQ ID NO 25
<211> LENGTH: 28
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Acylation with butyric acid

<400> SEQUENCE: 25

```
Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25
```

<210> SEQ ID NO 26
<211> LENGTH: 28
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Acylation with hexanoic acid

<400> SEQUENCE: 26

```
Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25
```

<210> SEQ ID NO 27
<211> LENGTH: 28
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Acylation with decanoic acid

<400> SEQUENCE: 27

```
Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25
```

<210> SEQ ID NO 28
<211> LENGTH: 28

```
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Acylation with Lauric acid

<400> SEQUENCE: 28

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 29
<211> LENGTH: 28
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Acylation with palmitic acid

<400> SEQUENCE: 29

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 30
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with 3-phenylpropionic acid

<400> SEQUENCE: 30

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 31
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with 3-octenoic acid

<400> SEQUENCE: 31

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 32
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Alkylation with octane
```

```
<400> SEQUENCE: 32

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 33
<211> LENGTH: 28
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Alkylation with octane

<400> SEQUENCE: 33

Gly Ser Cys Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 34
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid

<400> SEQUENCE: 34

Gly Ser Ser Phe Leu Ser Pro Glu His Gln Arg Val Gln Gln Arg
1               5                   10                  15

<210> SEQ ID NO 35
<211> LENGTH: 27
<212> TYPE: PRT
<213> ORGANISM: Rattus norvegicus
<220> FEATURE:
<221> NAME/KEY: MOD_RES
<222> LOCATION: (3)..(3)
<223> OTHER INFORMATION: Acylation with octanoic acid

<400> SEQUENCE: 35

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 36
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid

<400> SEQUENCE: 36

Gly Ser Ser Phe Leu Ser Pro Glu His Gln Arg
1               5                   10

<210> SEQ ID NO 37
<211> LENGTH: 10
<212> TYPE: PRT
<213> ORGANISM: Homo sapiens
```

```
<220> FEATURE:
<221> NAME/KEY: MOD_RES
<222> LOCATION: (3)..(3)
<223> OTHER INFORMATION: Acylation with octanoic acid

<400> SEQUENCE: 37

Gly Ser Ser Phe Leu Ser Pro Glu His Gln
1               5                   10

<210> SEQ ID NO 38
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (8)..(8)
<223> OTHER INFORMATION: AMIDATION

<400> SEQUENCE: 38

Gly Ser Ser Phe Leu Ser Pro Glu
1               5

<210> SEQ ID NO 39
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (7)..(7)
<223> OTHER INFORMATION: AMIDATION

<400> SEQUENCE: 39

Gly Ser Ser Phe Leu Ser Pro
1               5

<210> SEQ ID NO 40
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (6)..(6)
<223> OTHER INFORMATION: AMIDATION

<400> SEQUENCE: 40

Gly Ser Ser Phe Leu Ser
1               5

<210> SEQ ID NO 41
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid

<400> SEQUENCE: 41
```

```
Gly Ser Ser Phe Leu
1               5

<210> SEQ ID NO 42
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (5)..(5)
<223> OTHER INFORMATION: AMIDATION

<400> SEQUENCE: 42

Gly Ser Ser Phe Leu
1               5

<210> SEQ ID NO 43
<211> LENGTH: 4
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (4)..(4)
<223> OTHER INFORMATION: AMIDATION

<400> SEQUENCE: 43

Gly Ser Ser Phe
1

<210> SEQ ID NO 44
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (8)..(8)
<223> OTHER INFORMATION: AMIDATION

<400> SEQUENCE: 44

Gly Ser Ser Phe Leu Ser Pro Lys
1               5

<210> SEQ ID NO 45
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (8)..(8)
<223> OTHER INFORMATION: AMIDATION

<400> SEQUENCE: 45

Gly Ser Ser Phe Leu Ser Pro Arg
1               5
```

```
<210> SEQ ID NO 46
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (6)..(6)
<223> OTHER INFORMATION: AMIDATION

<400> SEQUENCE: 46

Gly Ser Ser Phe Leu Lys
1               5

<210> SEQ ID NO 47
<211> LENGTH: 5
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (5)..(5)
<223> OTHER INFORMATION: AMIDATION

<400> SEQUENCE: 47

Gly Ser Ser Phe Lys
1               5

<210> SEQ ID NO 48
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Acylation with octanoic acid
<220> FEATURE:
<221> NAME/KEY: MOD_RES
<222> LOCATION: (1)..(1)
<223> OTHER INFORMATION: N-Aminopentanoyl (NH2-(CH2)4-CO-) modification
<220> FEATURE:
<221> NAME/KEY: MOD_RES
<222> LOCATION: (5)..(5)
<223> OTHER INFORMATION: AMIDATION

<400> SEQUENCE: 48

Ser Phe Leu Ser Pro
1               5

<210> SEQ ID NO 49
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (7)..(7)
<223> OTHER INFORMATION: AMIDATION

<400> SEQUENCE: 49

Gly Leu Ser Phe Leu Ser Pro
1               5
```

```
<210> SEQ ID NO 50
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (7)..(7)
<223> OTHER INFORMATION: AMIDATION

<400> SEQUENCE: 50

Gly His Ser Phe Leu Ser Pro
1               5

<210> SEQ ID NO 51
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (7)..(7)
<223> OTHER INFORMATION: AMIDATION

<400> SEQUENCE: 51

Gly Lys Ser Phe Leu Ser Pro
1               5

<210> SEQ ID NO 52
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Alkylation with octane
<220> FEATURE:
<221> NAME/KEY: MOD_RES
<222> LOCATION: (7)..(7)
<223> OTHER INFORMATION: AMIDATION

<400> SEQUENCE: 52

Gly Ser Cys Phe Leu Ser Pro
1               5

<210> SEQ ID NO 53
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Alkylation with octane
<220> FEATURE:
<221> NAME/KEY: MOD_RES
<222> LOCATION: (7)..(7)
<223> OTHER INFORMATION: AMIDATION

<400> SEQUENCE: 53

Gly Ser Ser Phe Leu Ser Pro
1               5

<210> SEQ ID NO 54
```

```
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: O-Heptyl (O-C7H15) modification

<400> SEQUENCE: 54

Gly Ser Asp Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 55
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: NH-Heptyl (NH-C7H15) modification

<400> SEQUENCE: 55

Gly Ser Asp Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 56
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Xaa is -NH-(L-)CH(CH2NHCO-C7H15)-CO-

<400> SEQUENCE: 56

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 57
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: S-Heptyl (S-C7H15) modification

<400> SEQUENCE: 57

Gly Ser Cys Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 58
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Xaa is -NH-CH(n-C10H21)-CO-
```

-continued

```
<400> SEQUENCE: 58

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 59
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid

<400> SEQUENCE: 59

Gly Ser Thr Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 60
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid

<400> SEQUENCE: 60

Gly Leu Thr Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 61
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid

<400> SEQUENCE: 61

Gly Ser Lys Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 62
<211> LENGTH: 28
<212> TYPE: PRT
<213> ORGANISM: Homo sapiens

<400> SEQUENCE: 62

Gly Ser Trp Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 63
```

<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Xaa is Cha

<400> SEQUENCE: 63

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 64
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Xaa is (L-)Nal

<400> SEQUENCE: 64

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 65
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Benzyl (CH2-C6H5) modification

<400> SEQUENCE: 65

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 66
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Trityl (C(Ph)3) modification

<400> SEQUENCE: 66

Gly Ser Cys Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 67
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: 4-Methylpentanoyl (-CO-CH2CH2CH(CH3)2)

modification

<400> SEQUENCE: 67

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 68
<211> LENGTH: 7
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acylation with octanoic acid
<220> FEATURE:
<221> NAME/KEY: MOD_RES
<222> LOCATION: (7)..(7)
<223> OTHER INFORMATION: AMIDATION

<400> SEQUENCE: 68

Gly Ser Ser Phe Leu Ser Lys
1               5

<210> SEQ ID NO 69
<211> LENGTH: 5
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Xaa is Aib
<220> FEATURE:
<221> NAME/KEY: MOD_RES
<222> LOCATION: (3)..(3)
<223> OTHER INFORMATION: Alkylation with octane
<220> FEATURE:
<221> NAME/KEY: MOD_RES
<222> LOCATION: (5)..(5)
<223> OTHER INFORMATION: AMIDATION

<400> SEQUENCE: 69

Xaa His Ser Phe Lys
1               5

1

PREVENTIVES OR REMEDIES FOR HEPATOPATHY

CROSS-REFERENCE TO RELATED APPLICATIONS

This application is the U.S. national phase application of PCT International Application No. PCT/JP2004/006365, filed on Apr. 30, 2004, which claims the benefit of Japanese Application No. 2003-126088, filed Apr. 30, 2003, the disclosures of each of which are herein incorporated by reference in their entireties.

BACKGROUND OF THE INVENTION

(i) Field of the Invention

SEQUENCE LISTING

The sequence listing in the file named "69740o000004.txt" having a size of 28032 bytes that was created Jun. 17, 2009 is hereby incorporated by reference in its entirety.

The present invention relates to a therapeutic agent for hepatopathy. More particularly, the present invention relates to a medicament which contains, as an effective ingredient, a polypeptide derivative having an activity of binding to growth hormone secretagogue receptor (hereinafter, abbreviated as GHS-R) and thus elevating intracellular calcium ion concentration, and is useful for treating or preventing hepatic diseases such as hepatitis, liver cirrhosis and hepatic insufficiency, or for recovering hepatic regeneration and hepatic function or for promoting the recovery-after hepatectomy.

(ii) Description of the Related Art

Liver is an indispensable organ for life maintenance which plays an important role in the metabolism of many substances. Through regulating system in living bodies, liver has important function in order to maintain homeostasis in a blood level of sugar and lipids, and supplies energy to all tissues of a living body. Further, liver synthesizes many peptides, and deliver them to blood and tissue. Thus, liver has extremely important function in life maintenance, such as biological substance metabolism such as sugar metabolism, amino acids/protein metabolism, and lipid metabolism, excretion of metabolites, detoxication of chemical substances such as ammonia, and storage of vitamins.

In the liver, it is known that hepatitis is developed as a cause of virus infection, alcohol intake and drug intake, and when the hepatitis becomes chronic, a part thereof is shifted to liver cirrhosis, and its mortality is increased. It is known that, in patients with hepatopathy such as hepatitis, liver cirrhosis and hepatic insufficiency, decrease in fibrinogen, decrease in platelet, prolongation of blood coagulation time, and increase in serum enzymes released from the liver are occurred-accompanying with reduction in hepatic function. For this reason, a bleeding tendency appears, and this is a cause leading to death of patients (Non-Patent Literature 1). Currently, glycyrrhizin, glutathione, and vitamins are used for improving hepatic function, but a therapeutic suitable for treating hepatopathy diseases such as chronic hepatitis, alcoholic hepatopathy, fatty liver, liver cirrhosis and hepatic insufficiency has not yet been developed, and diet therapy by taking a high protein/high calorie food is mainly applied. Two million patients are suffering from hepatic diseases in Japan, two thousands patients die of liver cancers via liver cirrhosis in a year, but there is no effective therapeutical method. For viral hepatitis, interferon is used frequently, but interferon is not effective to all hepatitis patients, but severe side effect such as suicide is frequently manifested, becoming problematic.

For hepatic diseases, in addition to the aforementioned drug therapy, internal drug treatment such as percutaneous ethanol injection, microwave ablation and embolization of hepatic artery is performed, or surgical treatment such as hepatectomy and living-donor liver transplantation is performed, and either treatment of them is performed currently. Selection of an internal or a surgical treatment by a physician depends on an age and physical conditions of patients, for example, the state of diseases such as the size and the number of cancers, and hepatic function, determined case by case in a medical field, and internal drug treatment usually preceedes. When surgical treatment is performed, treatment is on a premise that the number of cancers is limited within a few, and remaining hepatic function is retained. Whether internal drug treatment is selected or surgical treatment is selected, reduction or abnormality in hepatic function is observed in many cases after these treatments. Particularly, in the case of living-donor liver transplantation, reduction or abnormality in hepatic function is frequently seen after transplantation operation in both of a donor and a recipient. Currently, for such reduction or abnormality in hepatic function after liver operation, nutrient state is managed, but the management does not prevent the reduction or the abnormality, and effective therapy for preventing or decreasing reduction or abnormality in hepatic function after liver operation is demanded.

Using a hepatic fibrosis or liver cirrhosis animal model, suppression of the hepatic fibrosis has been reported in hepatocyte growth factor (HGF) (Non-Patent Literature 2, Non-Patent Literature 3), or interferon α, β and γ (Non-Patent Literature 4). Since HGF has the angiogenic activity, side effect related with angiogenesis is concerned. In addition, it is reported that growth hormone (GH) acts on liver, and stimulates production of Insulin-like Growth Factor-1 (IGF-1), thereby to induce hepatocyte proliferation activity (Non-Patent Literature 5, Non-Patent Literature 6), and induces HGF by acting IGF-1 on hepatocyte (Non-Patent Literature 7), but there is no work in which therapeutic effect of GH for hepatopathy is studied. In addition, side effects such as edema, and deterioration of insulin resistance has been recognized. Further, it has been shown that insulin and Epidermal Growth Factor (EGF) (Non-Patent Literature 8), and Transforming Growth Factor-α (TGF-α) (Non-Patent Literature 9) also have hepatocyte proliferation activity (uptake of thymidine into DNA), but their effect on the improvement of hepatopathy is not clear.

On the other hand, ghrelin is a peptide consisting of 28 amino acids residues which were found in the stomach, and the serine residue at position 3 is modified with an octanoyl group (Patent Literature 1). It is shown that ghrelin acts on Growth Hormone Secretagogue-Receptor (GHS-R) (Non-Patent Literature 10), and is an endogenous brain-gut hormone which stimulates GH secretion from pituitary gland (Non-Patent Literature 11), and recently, it is further shown in mice or rats that ghrelin stimulates appetite and, by subcutaneous administration, ghrelin increased body weight and body fat (Non-Patent Literature 12, Non-Patent Literature 13, Non-Patent Literature 14). However, it is not known that ghrelin is used as an agent for preventing or treating hepatopathy.

Non-Patent Literature 1: "Internal drug Book 3" supervised by Yuichi Murakami, Kazu Yoshimura, 1987, published by Nakayama-Shoten Co., Ltd.

Non-Patent Literature 2: Matsuda et. al., "Preventive and therapeutic effects in rats of hepatocyte growth factor infusion on liver fibrosis/cirrhosis", Hepatology, vol. 26, No. 1, p. 81-89 (1997)

Non-Patent Literature 3: Takahiro Ueki et. al., "Hepatocyte growth factor gene therapy of liver cirrhosis in rats", Nature Drug, vol. 5, p. 226-230 (1999)

Non-Patent Literature 4: Hironori Taniguchi et al., "Hepatic Fibrosis Suppression Mechanism of Interferon", Advanced drug, vol. 55, p. 1803-1806 (2000)

Non-Patent Literature 5: Asakawa et. al., Journal of Endocrinology Investment, vol. 12, p. 343-347 (1989)

Non-Patent Literature 6: Ekberg et. al., Journal of Endocrinology, vol. 135, p. 59-67 (1992)

Non-Patent Literature 7: Skrtic et. al., Endocrinology, vol. 138, p. 4683-4689 (1997)

Non-Patent Literature 8: Richman et. al., Proceedings of the National Academy of Sciences, USA, vol. 73, p. 3589-3593 (1976)

Non-Patent Literature 9: E. M. Webber et. al., "In vivo response of hepatocytes to growth factors requires an initial priming stimulus", Hepatology, vol. 19, No. 2, p. 489-497 (1994)

Non-Patent Literature 10: Andrew D. Howard et. al., "A Receptor in Pituitary and Hypothalamus That Functions in Growth Hormone Release", Science, vol. 273, p. 974-977 (1996)

Non-Patent Literature 11: Masayasu Kojima et. al., "Ghrelin is a growth-hormone-releasing acylated peptide from stomach", Nature, vol. 402, p. 656-659 (1999)

Non-Patent Literature 12: Wren et. al., Endocrinology, vol. 141, p. 4325-4328 (2000)

Non-Patent Literature 13: Masamitsu Nakazato et. al., "A role for ghrelin in the central regulation of feeding", Nature, vol. 409, p. 194-198 (2001)

Non-Patent Literature 14: Mitsuyo Shintani et. al., "Ghrelin, an Endogenous Growth Hormone Secretagogue, Is a Novel Orexigenic Peptide That Antagonizes Leptin Action Through the Activation of Hypothalamic Neuropeptide Y/Y1 Receptor Pathway", Diabetes, vol. 50, p. 227-232 (2001)

Patent Literature 1: WO 01/07475

SUMMARY AND OBJECTS OF THE INVENTION

An object of the present invention is to provide a preventive or a therapeutic agent for hepatopathy. More particularly, an object of the present invention is to provide a drug suitable for treating or preventing hepatic diseases such as hepatitis, liver cirrhosis and hepatic insufficiency. Further, an object of the present invention is to provide a drug having a hepatocyte proliferation promoting activity which can be used as an agent for promoting hepatic regeneration and hepatic function recovery after hepatectomy.

In order to attain the aforementioned object, the present inventors have intensively studied, and obtained findings that a polypeptide derivative having an activity of binding to GHS-R and thus elevating intracellular calcium ion concentration has effects of preventing, alleviating progression of, or treating hepatic diseases such as hepatitis, liver cirrhosis and hepatic insufficiency. Further, the present inventors have found that such polypeptide derivatives have an activity of promoting hepatocyte proliferation and, as a result, is useful for arresting reduction in hepatic function after liver operation, preventing hepatic function abnormality or recovering hepatic regeneration and hepatic function. The present inventors have further studied, and completed the present invention.

That is, the present invention relates to:

(1) a preventive or a therapeutic agent for hepatopathy, comprising, as an effective ingredient, a polypeptide derivative having an activity of binding to GHS-R and thus elevating intracellular calcium ion concentration, and comprising one amino acid sequence selected from the group consisting of amino acid sequences represented by SEQ ID NOS: 1 to 22, or an amino acid sequence in which one to several amino acids are deleted, substituted or added at the position other than the first to fourth amino acid residues from the amino-terminus in the said amino acid sequence, or a pharmacologically acceptable salt thereof, (2) the preventive or the therapeutic agent for hepatopathy according to (1), wherein the polypeptide derivative is a polypeptide derivative in which, in a polypeptide amino acid sequence of comprising one amino acid sequence selected from the group consisting of amino acid sequences represented by SEQ ID NOS: 1 to 22 and an amino acid sequence in which one to several amino acids are deleted, substituted or added at the position other than the first to fourth amino acid residues in the said amino acid sequences, the second or third amino acid residue from the amino-terminus has a group represented by the following formula (1);

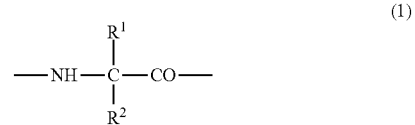

{wherein $R^1$ and $R^2$ are the same or different, and represent $-T^1-P^1-Q^1$ (wherein $T^1$ represents a divalent hydrocarbon group of 1 to 20 carbon atoms, $P^1$ represents $-CO-$, $-SO_2-$, $-CO-O-$, $-O-CO-$, $-O-$, $-CO-S-$, $-S-CO-$, $-CS-S-$, $-S-CS-$, $-S-$, $-CO-NR^4-$, $-NR^4-CO-$, $-CO-NR^4-CO-$, $-CS-NR^4-CS-$, $-S-S-$, $-CS-NR^4-$ or $-NR^4-CS-$ ($R^4$ represents a hydrogen atom or a $C_{1-4}$ alkyl group), and $Q^1$ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group), $-P^1-Q^1$ (wherein $P^1$ and $Q^1$ are the same as defined above) or $-Q^1$ (wherein $Q^1$ is the same as defined above), provided that when one of $R^1$ and $R^2$ is $Q^1$, the other represents $-T^1-P^1-Q^1$ (wherein $T^1$, $P^1$ and $Q^1$ are the same as defined above) or $-P^1-Q^1$ (wherein $P^1$ and $Q^1$ are the same as defined above)}, and which has an activity of binding to GHS-R and thus elevating intracellular calcium ion concentration, or a pharmacologically acceptable salt thereof, (3) the preventive or the therapeutic agent for hepatopathy according to (2), wherein the second or third amino acid residue from the amino-terminus has a group represented by the formula (2);

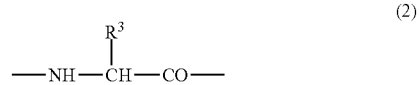

{wherein R³ represents -T²-P²-Q² (wherein T² represents a C₁₋₆ alkylene group, a C₂₋₆ alkenylene group, or a C₁₋₄ alkylene-phenylene group, P² represents —CO—O—, —O—CO—, —O—, —S—, —S—S—, —CO—NR⁴— or —NR⁴—CO— (R⁴ represents a hydrogen atom or a C₁₋₄ alkyl group), and Q² represents an optionally substituted C₁₋₂₀ alkyl group, an optionally substituted C₂₋₂₀ alkenyl group, an optionally substituted C₃₋₈ cycloalkyl group, an optionally substituted C₁₋₆ alkylene-C₃₋₈ cycloalkyl group, an optionally substituted C₆₋₁₄ aryl group or an optionally substituted C₇₋₁₆ aralkyl group) or -P²-Q² (wherein P² and Q² are the same as defined above)}, (4) the preventive or the therapeutic agent for hepatopathy according to (3), wherein T² is a C₁₋₆ alkylene group, P² is —O—CO—, and Q² is an optionally substituted C₁₋₂₀ alkyl group, (5) the preventive or the therapeutic agent for hepatopathy according to (4), wherein T² is methylene or ethylene, P² is —O—CO—, and Q² is a C₁₋₂₀ alkyl group, (6) the preventive or the therapeutic agent for hepatopathy according to (5), wherein Q² is a C₇ alkyl group, (7) the preventive or the therapeutic agent for hepatopathy according to any one of (2) to (6), wherein the amino acid sequences of SEQ ID NOS: 1 to 22 are any one of the amino acid sequences of SEQ ID NOS: 1 to 10 or 22, (8) a preventive or a therapeutic agent for hepatopathy, comprising, as an effective ingredient, a polypeptide derivative represented by the formula (3); X—Y—Z (wherein X represents an organic group having a molecular chain length corresponding to an amino acid residue, a dipeptide or a tripeptide, and comprising one or more kinds of atoms selected from the group consisting of C, H, O, N and S, Y represents a group represented by the following formula (1);

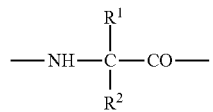

{wherein R¹ and R² are the same or different, and represent -T¹-P¹-Q¹ (wherein T¹ represents a divalent hydrocarbon group of 1 to 20 carbon atoms, P¹ represents, —CO—, —SO₂—, —CO—O—, —O—CO—, —O—, —CO—S—, —S—CO—, —CS—S—, —S—CS—, —S—, —CO—NR⁴—, —NR⁴—CO—, —CO—NR⁴—CO—, —CS—NR⁴—CS—, —S—S—, —CS—NR⁴— or —NR⁴—CS— (R⁴ represents a hydrogen atom or a C₁₋₄ alkyl group), and Q¹ represents a hydrogen atom, an optionally substituted C₁₋₃₅ alkyl group, an optionally substituted C₂₋₃₅ alkenyl group, an optionally substituted C₃₋₈ cycloalkyl group, an optionally substituted C₁₋₆ alkylene-C₃₋₈ cycloalkyl group, an optionally substituted C₆₋₁₄ aryl group or an optionally substituted C₇₋₁₆ aralkyl group), -P¹-Q¹ (wherein P¹ and Q¹ are the same as defined above) or -Q¹ (wherein Q¹ is the same as defined above), provided that when one of R¹ and R² is Q¹, the other represents -T¹-P¹-Q¹ (wherein T¹, P¹ and Q¹ are the same as defined above) or -P¹-Q¹ (wherein P¹ and Q¹ are the same as defined above), Z represents a natural amino acid residue or an optical isomer thereof}, and having an activity of binding to GHS-R and thus elevating intracellular calcium ion concentration, or a pharmaceutically acceptable salt thereof, (9) a preventive or a therapeutic agent for hepatopathy, comprising, as an effective ingredient, a polypeptide derivative in which a partial amino acid sequence corresponding to an amino acid sequence of the fifth amino acid from the amino-terminus to the carboxyl-terminus in one amino acid sequence selected from the group consisting of amino acid sequences represented by SEQ ID NOS: 1 to 22, or an amino acid sequence in which one to several amino acids are deleted, substituted or added in the said partial amino acid sequence is bound to a polypeptide derivative represented by the formula (3); X—Y—Z (wherein X represents an organic group having a molecular chain length corresponding to an amino acid residue, a dipeptide or a tripeptide, and comprising one or more kinds of atoms selected from the group consisting of C, H, O, N and S, Y represents a group represented by the following formula (1);

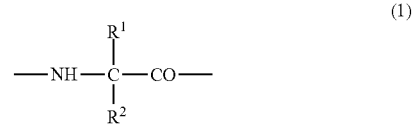

{wherein R¹ and R² are the same or different, and represent -T¹-P¹-Q¹ (wherein T¹ represents a divalent hydrocarbon group of 1 to 20 carbon atoms, P¹ represents, —CO—, —SO₂—, —CO—O—, —O—CO—, —O—, —CO—S—, —S—CO—, —CS—S—, —S—CS—, —S—, —CO—NR⁴—, —NR⁴—CO—, —CO—NR⁴—CO—, —CS—NR⁴—CS—, —S—S—, —CS—NR⁴— or —NR⁴—CS— (R⁴ represents a hydrogen atom or a C₁₋₄ alkyl group), and Q¹ represents a hydrogen atom, an optionally substituted C₁₋₃₅ alkyl group, an optionally substituted C₂₋₃₅ alkenyl group, an optionally substituted C₃₋₈ cycloalkyl group, an optionally substituted C₁₋₆ alkylene-C₃₋₈ cycloalkyl group, an optionally substituted C₆₋₁₄ aryl group or an optionally substituted C₇₋₁₆ aralkyl group), -P¹-Q¹ (wherein P¹ and Q¹ are the same as defined above) or -Q¹ (wherein Q¹ is the same as defined above), provided that when one of R¹ and R² is Q¹, the other represents -T¹-P¹-Q¹ (wherein T¹, P¹ and Q¹ are the same as defined above) or -P¹-Q¹ (wherein P¹ and Q¹ are the same as defined above), Z represents a natural amino acid residue or an optical isomer thereof}, and which has an activity of binding to GHS-R and thus elevating intracellular calcium ion concentration, or a pharmacologically acceptable salt thereof,

(10) the preventive or the therapeutic agent for hepatopathy according to (8) or (9), wherein X is represented by the formula (4); H₂N—X¹—CO— (X¹ represents a C₄ alkylene group optionally having a substituent, or an organic group in which at least one carbon atom of the C₄ alkylene group is substituted with O, N or S),

(11) a preventive or a therapeutic agent for hepatopathy, comprising, as an effective ingredient, a polypeptide derivative represented by the formula (5); A-B-C-D (wherein A and D are a natural amino acid residue or an optical isomer thereof, one or both of B and C represent(s) a group represented by the following formula (1);

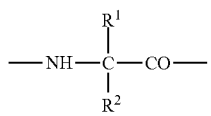

{wherein $R^1$ and $R^2$ are the same or different, and represent -$T^1$-$P^1$-$Q^1$ (wherein $T^1$ represents a divalent hydrocarbon group of 1 to 20 carbon atoms, $P^1$ represents —CO—, —$SO_2$—, —CO—O—, —O—CO—, —O—, —CO—S—, —S—CO—, —CS—S—, —S—CS—, —S—, —CO—$NR^4$—, —$NR^4$—CO—, —CO—$NR^4$—CO—, —CS—$NR^4$—CS—, —S—S—, —CS—$NR^4$— or —$NR^4$—CS— ($R^4$ represents a hydrogen atom or a $C_{1-4}$ alkyl group), and $Q^1$ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group), -$P^1$-$Q^1$ (wherein $P^1$ and $Q^1$ are the same as defined above) or -$Q^1$ (wherein $Q^1$ is the same as defined above), provided that when one of $R^1$ and $R^2$ is $Q^1$, the other represents $T^1$-$P^1$-$Q^1$ (wherein $T^1$, $P^1$ and $Q^1$ are the same as defined above) or -$P^1$-$Q^1$ (wherein $P^1$ and $Q^1$ are the same as defined above), when only one of B and C is an amino acid residue represented by the formula (1), the other is a natural amino acid residue or an optical isomer thereof}, and having an activity of binding to GHS-R and thus elevating intracellular calcium ion concentration, or a pharmacologically acceptable salt thereof,

(12) a preventive or a therapeutic agent for hepatopathy, comprising, as an effective ingredient, a polypeptide derivative in which a partial amino acid sequence corresponding to an amino acid sequence of the fifth amino acid from the amino-terminus to the carboxyl-terminus in one amino acid sequence selected from the group consisting of amino acid sequences represented by SEQ ID NOS: 1 to 12, or an amino acid sequence in which one to several amino acids are deleted, substituted or added in the said partial amino acid sequence is bound to a polypeptide derivative represented by the formula (5); A-B-C-D [wherein A and D are a natural amino acid residue or an optical isomer thereof, one or both of B and C represent(s) a group represented by the following formula (1);

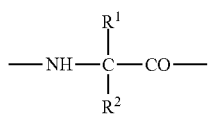

{wherein $R^1$ and $R^2$ are the same or different, and represent -$T^1$-$P^1$-$Q^1$ (wherein $T^1$ represents a divalent hydrocarbon group of a carbon number of 1 to 20, $P^1$ represents —CO—, —$SO_2$—, —CO—O—, —O—CO—, —O—, —CO—S—, —S—CO—, —CS—S—, —S—CS—, —S—, —CO—$NR^4$—, —$NR^4$—CO—, —CO—$NR^4$—CO—, —CS—$NR^4$—CS—, —S—S—, —CS—$NR^4$— or —$NR^4$—CS— ($R^4$ represents a hydrogen atom or a $C_{1-4}$ alkyl group), and $Q^1$ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group), -$P^1$-$Q^1$ (wherein $P^1$ and $Q^1$ are the same as defined above) or -$Q^1$ (wherein $Q^1$ is the same as defined above), provided that when one of $R^1$ and $R^2$ is $Q^1$, the other represents -$T^1$-$P^1$-$Q^1$ (wherein $T^1$, $P^1$ and $Q^1$ are the same as defined above) or -$P^1$-$Q^1$ (wherein $P^1$ and $Q^1$ are the same as defined above)}, and when only one of B and C is an amino acid residue represented by the formula (1), the other is a natural amino acid residue or an optical isomer thereof], and which has an activity of binding to GHS-R and thus elevating intracellular calcium ion concentration, or a pharmacologically acceptable salt thereof,

(13) the preventive or the therapeutic agent for hepatopathy according to anyone of (1) to (12), wherein a basic amino acid is further bound to the carboxyl-terminus,

(14) the preventive or the therapeutic agent for hepatopathy according to any one of (1) to (13), wherein the carboxyl group at the carboxyl-terminus forms a salt, ester or amide,

(15) the preventive or the therapeutic agent for hepatopathy according to any one of (1) to (14), wherein the hepatopathy is one or more diseases selected from the group consisting of hepatitis, liver cirrhosis and hepatic insufficiency,

(16) the preventive or the therapeutic agent for hepatopathy according to (15), wherein the hepatitis is one or more diseases selected from the group consisting of viral hepatitis, alcoholic hepatitis, drug-induced hepatitis and autoimmune hepatitis,

(17) the preventive or the therapeutic agent for hepatopathy according to any one of (1) to (14), which is an agent for promoting hepatic regeneration and hepatic function recovery after hepatectomy,

(18) the preventive or the therapeutic agent for hepatopathy according to any one of (1) to (14), wherein the hepatopathy is a disease after liver transplantation, or

(19) the preventive or the therapeutic agent for hepatopathy according to any one of (1) to (18), wherein the dose per day is 0.001 to 100 mg.

In addition, the present invention relates to:

(20) a method for treating hepatopathy, comprising administering to a mammal including humans a polypeptide derivative having an activity of binding to GHS-R and thus elevating intracellular calcium ion concentration, wherein the polypeptide derivative comprises one amino acid sequence selected from the group consisting amino acid sequences represented by SEQ ID NOS: 1 to 22, or an amino acid sequence in which one to several amino acids are deleted, substituted, or added at the amino acid residues other than the first to fourth amino acid residues at the amino-terminus in the said amino acid sequence, or a salt thereof,

(21) a method for treating hepatopathy, comprising administering to a mammal including humans a polypeptide derivative which is represented by the formula (3); X—Y—Z [wherein X represents an organic group having a molecular chain length corresponding to an amino acid residue, a dipeptide or a tripeptide, and comprising one or more kinds of atoms selected from the group consisting of C, H, O, N and S, Y represents a group represented by the following formula (1);

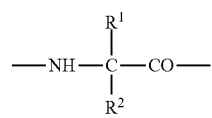

{wherein $R^1$ and $R^2$ are the same or different, and represent -$T^1$-$P^1$-$Q^1$ (wherein $T^1$ represents a divalent hydrocarbon group of 1 to 20 carbon atoms, $P^1$ represents —CO—, —$SO_2$—, —CO—O—, —O—CO—, —O—, —CO—S—, —S—CO—, —CS—S—, —S—CS—, —S—, —CO—$NR^4$—, —$NR^4$—CO—, —CO—$NR^4$—CO—, —CS—$NR^4$—CS—, —S—S—, —CS—$NR^4$— or —$NR^4$—CS— ($R^4$ represents a hydrogen atom or a $C_{1-4}$ alkyl group), $Q^1$ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group), -$P^1$-$Q^1$ (wherein $P^1$ and $Q^1$ are the same as defined above) or -$Q^1$ (wherein $Q^1$ is the same as defined above), provided that when one of $R^1$ and $R^2$ is $Q^1$, the other represents -$T^1$-$P^1$-$Q^1$ (wherein $T^1$, $P^1$ and $Q^1$ are the same as defined above) or -$P^1$-$Q^1$ (wherein $P^1$ and $Q^1$ are the same as defined above)}, Z represents a natural amino acid residue or an optical isomer thereof], and which has an activity of binding to GHS-R and thus elevating intracellular calcium ion concentration, or a pharmacologically acceptable salt thereof,

(22) a method for treating hepatopathy, comprising administering to a mammal including humans a polypeptide derivative in which a partial amino acid sequence corresponding to an amino acid sequence from the fifth amino acid from the amino-terminus to a carboxyl-terminus in one amino acid sequence selected from the group consisting of amino acid sequences represented by SEQ ID NOS: 1 to 22, or an amino acid sequence in which one to several amino acids are deleted, substituted or added in the said partial amino acid sequence is bound to a polypeptide derivative represented by the formula (3); X—Y—Z (wherein X represents an organic group having a molecular chain length corresponding to an amino acid residue, a dipeptide or a tripeptide, and comprising one or more kinds of atoms selected from the group consisting of C, H, O, N and S, Y represents a group represented by the following formula (1);

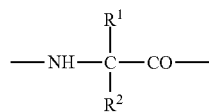

{wherein $R^1$ and $R^2$ are the same or different, and represent -$T^1$-$P^1$-$Q^1$ (wherein $T^1$ represents a divalent hydrocarbon group of 1 to 20 carbon atoms, $P^1$ represents —CO—, —$SO_2$—, —CO—O—, —O—CO—, —O—, —CO—S—, —S—CO—, —CS—S—, —S—CS—, —S—, —CO—$NR^4$—, —$NR^4$—CO—, —CO—$NR^4$—CO—, —CS—$NR^4$—CS—, —S—S—, —CS—$NR^4$— or —$NR^4$—CS— ($R^4$ represents a hydrogen atom or a $C_{1-4}$ alkyl group), and $Q^1$ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group), -$P^1$-$Q^1$ (wherein $P^1$ and $Q^1$ are the same as defined above) or -$Q^1$ (wherein $Q^1$ is the same as defined above), provided that when one of $R^1$ and $R^2$ is $Q^1$, the other represents -$T^1$-$P^1$-$Q^1$ (wherein $T^1$, $P^1$ and $Q^1$ are the same as defined above) or -$P^1$-$Q^1$ (wherein $P^1$ and $Q^1$ are the same as defined above), Z represents a natural amino acid residue or an optical isomer thereof)}, and which has an activity of binding to GHS-R and thus elevating intracellular calcium ion concentration, or a pharmacologically acceptable salt thereof.

(23) the method for treating hepatopathy according to (21) or (22), wherein X is represented by the formula (4); $H_2N$—$X^1$—CO— ($X^1$ represents a $C_4$ alkylene group optionally having a substituent, or an organic group in which at least one carbon atom of the $C_4$ alkylene group is substituted with O, N or S),

(24) a method for treating hepatopathy, comprising administering to a mammal including humans a polypeptide derivative represented by the formula (5); A-B-C-D {wherein A and D are a natural amino acid residue or an optical isomer thereof, one or both of B and C represent(s) a group represented by the following formula (1);

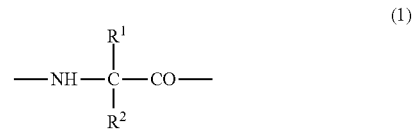

{wherein $R^1$ and $R^2$ are the same or different, and represent -$T^1$-$P^1$-$Q^1$ (wherein $T^1$ represents a divalent hydrocarbon group of 1 to 20 carbon atoms, $P^1$ represents —CO—, —$SO_2$—, —CO—O—, —O—CO—, —O—, —CO—S—, —S—CO—, —CS—S—, —S—CS—, —S—, —CO—$NR^4$—, —$NR^4$—CO—, —CO—$NR^4$—CO—, —CS—$NR^4$—CS—, —S—S—, —CS—$NR^4$— or —$NR^4$—CS— ($R^4$ represents a hydrogen atom or a $C_{1-4}$ alkyl group), and $Q^1$ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group), -$P^1$-$Q^1$ (wherein $P^1$ and $Q^1$ are the same as defined above) or -$Q^1$ (wherein $Q^1$ is the same as defined above), provided that when one of $R^1$ and $R^2$ is $Q^1$, the other represents -$T^1$-$P^1$-$Q^1$ (wherein $T^1$, $P^1$ an $Q^1$ are the same as defined above) or -$P^1$-$Q^1$ (wherein $P^1$ and $Q^1$ are the same as defined above), when only one of B and C is an amino acid residue represented by the formula (1), the other is a natural amino acid residue or an optical isomer thereof)}, and having an activity of binding to GHS-R and thus elevating intracellular calcium ion concentration, or a pharmacologically acceptable salt thereof,

(25) a method for treating hepatopathy, comprising administering to a mammal including humans a polypeptide derivative in which a partial amino acid sequence corresponding to an amino acid sequence from the fifth amino acid at the amino-terminus to the carboxyl-terminus in one amino acid sequence selected from the group consisting of amino acid sequences represented by SEQ ID NOS: 1 to 22, or an amino acid sequence in which one to several amino acids are deleted, substituted or added in the said partial amino acid sequence is bound to a polypeptide derivative represented by the formula (5); A-B-C-D {wherein A and D are a natural amino acid residue or an optical isomer thereof, one or both of B and C represent(s) a group represented by the following formula (1);

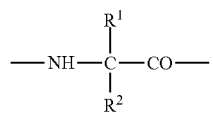

(1)

wherein R¹ and R² are the same or different, and represents -T¹-P¹-Q¹ (wherein T¹ represents a divalent hydrocarbon group of 1 to 20 carbon atoms, P¹ represents —CO—, —SO$_2$—, —CO—O—, —O—CO—, —O—, —CO—S—, —S—CO—, —CS—S—, —S—CS—, —S—, —CO—NR⁴—, —NR⁴—CO—, —CO—NR⁴—CO—, —CS—NR⁴—CS—, —S—S—, —CS—NR⁴— or —NR⁴—CS— (R⁴ represents a hydrogen atom or a $C_{1-4}$ alkyl group), and Q¹ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group), -P¹-Q¹ (wherein P¹ and Q¹ are the same as defined above), or -Q¹ (wherein Q¹ is the same as defined above), provided that when one of R¹ and R² is Q¹, the other represents -T¹-P¹-Q¹ (wherein T¹, P¹ and Q¹ are the same as defined above) or -P¹-Q¹ (wherein P¹ and Q¹ are the same as defined above), when only one of B and C is an amino acid residue represented by the formula (1), the other is a natural amino acid residue or an optical isomer thereof)}, and has an activity of binding to GHS-R and thus elevating intracellular calcium ion concentration, a pharmacologically acceptable salt thereof,

(26) the method for treating hepatopathy according to any one of (20) to (35), wherein a basic amino acid is further bound to the carboxyl-terminus,

(27) the method for treating hepatopathy according to any one of (20) to (26), wherein the carboxyl group at the carboxyl-terminus forms a salt, ester or amide,

(28) the method for treating hepatopathy according to any of (20) to (27), wherein the hepatopathy is one or more diseases selected from the group consisting of hepatitis, liver cirrhosis and hepatic insufficiency,

(29) the method for treating hepatopathy according to (28), the hepatitis is one or more diseases selected from the group consisting of viral hepatitis, alcoholic hepatitis, drug-induced hepatitis and autoimmune hepatitis,

(30) the method for treating hepatopathy according to any one of (20) to (27), which is an agent for promoting hepatic regeneration and hepatic function recovery after hepatectomy,

(31) the method for treating hepatopathy according to any one of (20) to (27), wherein the hepatopathy is a disease after liver transplantation, or

(32) the method for treating hepatopathy according to any one of (20) to (31), wherein the dose per day is 0.001 to 100 mg.

In addition, the present invention relates to:

(33) use of a polypeptide derivative having an activity of binding to GHS-R and thus elevating intracellular calcium ion concentration, and having an amino acid sequence selected from the group consisting of amino acid sequences represented by SEQ ID NOS: 1 to 22, or an amino acid sequence in which one to several amino acids are deleted, substituted or added at the position other than the first to fourth amino acid residues from the amino-terminus in the said amino acid sequence, or a salt thereof, for preparing a medicament for preventing or treating hepatopathy,

(34) use of a polypeptide derivative of a polypeptide represented by the formula (3); X—Y—Z {wherein X represents an organic group having a molecular chain length corresponding to an amino acid residue, a dipeptide or a tripeptide, and comprising one or more kinds of atoms selected from the group consisting of C, H, O, N and S, Y represents a group represented by the following formula (1);

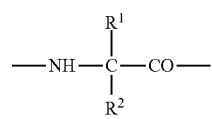

(1)

[wherein R¹ and R² are the same or different, and represent -T¹-P¹-Q¹ (wherein T¹ represents a divalent hydrocarbon group of 1 to 20 carbon atoms, P¹ represents —CO—, —SO$_2$—, —CO—O—, —O—CO—, —O—, —CO—S—, —S—CO—, —CS—S—, —S—CS—, —S—, —CO—NR⁴—, —NR⁴—CO—, —CO—NR⁴—CO—, —CS—NR⁴—CS—, —S—S—, —CS—NR⁴— or —NR⁴—CS— (R⁴ represents a hydrogen atom or a $C_{1-4}$ alkyl group), and Q¹ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group), -P¹-Q¹ (wherein P¹ and Q¹ are the same as defined above) or -Q¹ (wherein Q¹ is the same as defined above), provided that when one of R¹ and R² is Q¹, the other represents -T¹-P¹-Q¹ (wherein T¹, P¹ and Q¹ are the same as defined above) or -P¹-Q¹ (wherein P¹ and Q¹ are the same as defined above)], Z represents a natural amino acid residue or an optical isomer thereof}, and having an activity of binding to GHS-R and thus elevating intracellular calcium ion concentration, or a pharmacologically acceptable salt thereof, for preparing a medicament for preventing or treating hepatopathy,

(35) use of a polypeptide derivative in which a partial amino acid sequence corresponding to an amino acid sequence of the fifth amino acid from the amino-terminus to the carboxyl-terminus in an amino acid sequence selected from the group consisting of amino acid sequences represented by SEQ ID NOS: 1 to 22, or an amino acid sequence in which one to several amino acids are deleted, substituted or added in the said partial amino acid sequence is bound to a polypeptide derivative represented by the formula (3); X—Y—Z {wherein X represents an organic group having a molecular chain length corresponding to an amino acid residue, a dipeptide or tripeptide, and comprising one or more kinds of atoms selected from the group consisting of C, H, O, N and S, Y represents a group represented by the following formula (1);

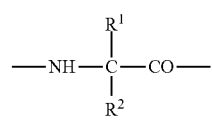

(1)

{wherein $R^1$ and $R^2$ are the same or different, and represent -$T^1$-$P^1$-$Q^1$ (wherein $T^1$ represents a divalent hydrocarbon group of 1 to 20 carbon atoms, $P^1$ represents —CO—, —$SO_2$—, —CO—O—, —O—CO—, —O—, —CO—S—, —S—CO—, —CS—S—, —S—CS—, —S—, —CO—$NR^4$—, —$NR^4$—CO—, —CO—$NR^4$—CO—, —CS—$NR^4$—CS—, —S—S—, —CS—$NR^4$— or —$NR^4$—CS— ($R^4$ represents a hydrogen atom or a $C_{1-4}$ alkyl group), and $Q^1$ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group), -$P^1$-$Q^1$ (wherein $P^1$ and $Q^1$ are the same as defined above) or -$Q^1$ (wherein $Q^1$ is the same as defined above), provided that, when one of $R^1$ and $R^2$ is $Q^1$, the other represents -$T^1$-$P^1$-$Q^1$ (wherein $T^1$, $P^1$ and $Q^1$ are the same as defined above) or -$P^1$-$Q^1$ (wherein $P^1$ and $Q^1$ are the same as defined above), Z represents a natural amino acid residue or an optical isomer thereof}, and which has an activity of binding to GHS-R and thus elevating intracellular calcium ion concentration, or a pharmacologically acceptable salt, for preparing a medicament for preventing or treating hepatopathy,

(36) the use according to (34) or (35), wherein X is represented by the formula (4); $H_2N$—$X^1$—CO— ($X^1$ represents a $C_4$ alkylene group optionally having a substituent, or an organic group in which at least one carbon atom of the $C_4$ alkylene group is substituted with O, N or S),

(37) use of a polypeptide derivative represented by the formula (5); A-B-C-D (wherein A and D are a natural amino acid residue or an optical isomer thereof, one or both of B and C is/are represented by the following formula (1);

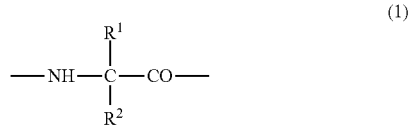

(1)

{wherein $R^1$ and $R^2$ are the same or different, and represent-$T^1$-$P^1$-$Q^1$ (wherein $T^1$ represents a divalent hydrocarbon group of 1 to 20 carbon atoms, $P^1$ represents —CO—, —$SO_2$—, —CO—O—, —O—CO—, —O—, —CO—S—, —S—CO—, —CS—S—, —S—CS—, —S—, —CO—$NR^4$—, —$NR^4$—CO—, —CO—$NR^4$—CO—, —CS—$NR^4$—CS—, —S—S—, —CS—$NR^4$— or —$NR^4$—CS— ($R^4$ represents a hydrogen atom or a $C_{1-4}$ alkyl group), and $Q^1$ represents a hydrogen atom, an optionally substituted $C_{1-35}$ alkyl group, an optionally substituted $C_{2-35}$ alkenyl group, an optionally substituted $C_{3-8}$ cycloalkyl, an optionally substituted $C_{1-6}$ alkylene-$C_{3-8}$ cycloalkyl group, an optionally substituted $C_{6-14}$ aryl group or an optionally substituted $C_{7-16}$ aralkyl group), -$P^1$-$Q^1$ (wherein $P^1$ and $Q^1$ are the same as defined above) or -$Q^1$ (wherein $Q^1$ is the same as defined above), provided that when one of $R^1$ and $R^2$ is $Q^1$, the other represents -$T^1$-$P^1$-$Q^1$ (wherein $T^1$, $P^1$ and $Q^1$ are the same as defined above) or -$P^1$-$Q^1$ (wherein $P^1$ and $Q^1$ are the same as defined above), when only one of B and C is an amino acid residue represented by the formula (1), the other is a natural amino acid residue or an optical isomer thereof}, and having an activity of binding to GHS-R and thus elevating intracellular calcium ion concentration, or a pharmacologically acceptable salt, for preparing a medicament for preventing or treating hepatopathy,

(38) use of a polypeptide derivative in which a partial amino acid sequence corresponding to an amino acid sequence of the fifth amino acid from the amino-terminus to the carboxyl-terminus in an amino acid sequence selected from the group consisting of amino acid sequences represented by SEQ ID NOS: 1 to 22, or an amino acid sequence in which one to several amino acids are deleted, substituted or added in the said partial amino acid sequence is bound to a polypeptide derivative represented by the formula (5); A-B-C-D (wherein A and D are a natural amino acid residue or an optical isomer thereof, one or both of B and C represent(s) a group represented by the following formula;

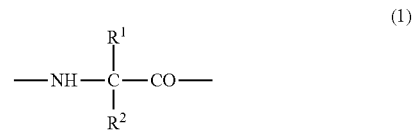

(1)

{wherein $R^1$ and $R^2$ are the same or different, and represent -$T^1$-$P^1$-$Q^1$ (wherein $T^1$ represents a divalent hydrocarbon group of 1 to 20 carbon atoms, $P^1$ represents —CO—, —$SO_2$—, —CO—O—, —O—CO—, —O—, —CO—S—, —S—CO—, —CS—S—, —S—CS—, —S—, —CO—$NR^4$—, —$NR^4$—CO—, —CO—$NR^4$—CO—, —CS—$NR^4$—CS—, —S—S—, —CS—$NR^4$— or —$NR^4$—CS— ($R^4$ represents a hydrogen atom or a $C_{1-4}$ alkyl group), and $Q^1$ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group), -$P^1$-$Q^1$ (wherein $P^1$ and $Q^1$ are the same as defined above) or -$Q^1$ (wherein $Q^1$ is the same as defined above), provided that when one of $R^1$ and $R^2$ is $Q^1$, the other represents $T^1$-$P^1$-$Q^1$ (wherein $T^1$, $P^1$ and $Q^1$ are the same as defined above), or -$P^1$-$Q^1$ (wherein $P^1$ and $Q^1$ are the same as defined above), when only one of B and C is an amino acid residue represented by the formula (1), the other is a natural amino acid residue or an optical isomer thereof}, and which has an activity of binding to GHS-R and thus elevating intracellular calcium ion concentration, or a pharmacologically acceptable salt, for preparing a medicament for preventing or treating hepatopathy,

(39) the use according to any one of (34) to (38), wherein a basic amino acid is further bound to the carboxyl-terminus,

(40) the use according to any one of (34) to (39), wherein the carboxyl group at a carboxyl-terminus forms a salt, ester or amide,

(41) the use according to any one of (34) to (40), wherein the hepatopathy is one or more diseases selected from the group consisting of hepatitis, liver cirrhosis and hepatic insufficiency,

(42) the use according (41), wherein the hepatitis is one or more diseases selected from the group consisting of viral hepatitis, alcoholic hepatitis, drug-induced hepatitis and autoimmune hepatitis,

(43) the use according to any one of (34) to (40), which is an agent for promoting hepatic regeneration and hepatic function recovery after hepatectomy,

(44) the use according to any one of (34) to (40), wherein the hepatopathy is a disease after liver transplantation, or

(45) the use according to any one of (34) to (44), wherein the dose per day is 0.001 to 100 mg.

In addition, the present invention relates to:

(46) a preventive or a therapeutic agent for hepatopathy, comprising a polypeptide derivative having an activity of binding to GHS-R and thus elevating intracellular calcium ion concentration, and comprising an amino acid sequence selected from the group consisting of amino acid sequences represented by SEQ ID NOS: 1 to 22, or an amino acid sequence in which one to several amino acids are deleted, substituted or added at the position other than the first to fourth amino acid residues from the amino-terminus in the said amino acid sequence, or a pharmacologically acceptable salt,

(47) the preventive or the therapeutic agent for hepatopathy according to (46), wherein the polypeptide derivative is a peptide comprising an amino acid sequence which is the first to fourth amino acid residues from the amino-terminus in an amino acid sequence selected from the group consisting of amino acid sequences represented by SEQ ID NOS: 1 to 22,

(48) the preventive or the therapeutic agent for hepatopathy according to (46), wherein the polypeptide derivative is a peptide comprising an amino acid sequence which is the first to tenth amino acid residues from the amino-terminus in an amino acid sequence selected from the group consisting of amino acid sequences represented by SEQ ID NOS: 1 to 22, or an amino acid sequence in which one to several amino acids are deleted, substituted or added at the position other than the first to fourth amino acid residues from the amino-terminus in the said amino acid sequence comprising ten amino acid residues,

(49) the preventive or the therapeutic agent for hepatopathy according to (46), wherein the polypeptide derivative is a peptide comprising an amino acid sequence which is the first to fifteenth amino acid residues from the amino-terminus in an amino acid sequence selected from the group consisting of amino acid sequences represented by SEQ ID NOS: 1 to 22, or an amino acid sequence in which one to several amino acids are deleted, substituted or added at the position other than the first to fourth amino acid residues from the amino-terminus in the said amino acid sequence comprising 15 amino acid residues.

In addition, the present invention relates to a preventive or a therapeutic agent for hepatopathy, comprising, as an effective ingredient, (a) a polypeptide derivative in which an amino acid residue at the second or third position from the amino-terminus in an amino acid sequence of the first to fourth amino acids from the amino-terminus of one amino acid sequence selected from amino acid sequences represented by SEQ ID NOS: 1 to 22 has the aforementioned formula (1), (b) a polypeptide derivative in which an amino acid residue at the second or third position from the amino-terminus in an amino acid sequence of the first to tenth amino acids from the amino-terminus of one amino acid sequence selected from amino acid sequences represented by SEQ ID NOS: 1 to 22 has the aforementioned formula (1), (c) a polypeptide derivative in which an amino acid residue at the second or third position from the amino-terminus in an amino acid sequence of the first to fifteenth amino acids from the amino-terminus of one amino acid sequence selected from amino acid sequences represented by SEQ ID NOS: 1 to 22 has the aforementioned formula (1), (d) a polypeptide derivative in which an amino acid residue at the second or third position from the amino-terminus in an amino acid sequence of the first to tenth amino acids from the amino-terminus, wherein one to several amino acids are deleted, substituted or added at the amino acid residue(s) other than the first to fourth amino acid residues from the amino-terminus of one amino acid sequence selected from amino acid sequences represented by SEQ ID NOS: 1 to 22 has the aforementioned formula (1), or (e) a polypeptide derivative in which an amino acid residue at the second or third position from the amino-terminus in an amino acid sequence of the first to fifteenth amino acids from the amino-terminus, wherein one to several amino acids are deleted, substituted or added at the amino acid residue(s) other than the first to fourth amino acid residues from the amino-terminus of one amino acid sequence selected from amino acid sequences represented by SEQ ID NOS: 1 to 22 has the aforementioned formula (1), which has an activity of binding to GHS-R and thus elevating intracellular calcium ion concentration, or a pharmacologically acceptable salt thereof, or a method for treating hepatopathy, comprising administering a polypeptide derivative according to any one of (a) to (e) to a mammal including humans, or use of a polypeptide derivative according to any one of (a) to (e) or a pharmacologically acceptable salt for preparing medicaments for preventing or treating hepatopathy.

DETAILED DESCRIPTION OF PREFERRED EMBODIMENTS

Figure 1:
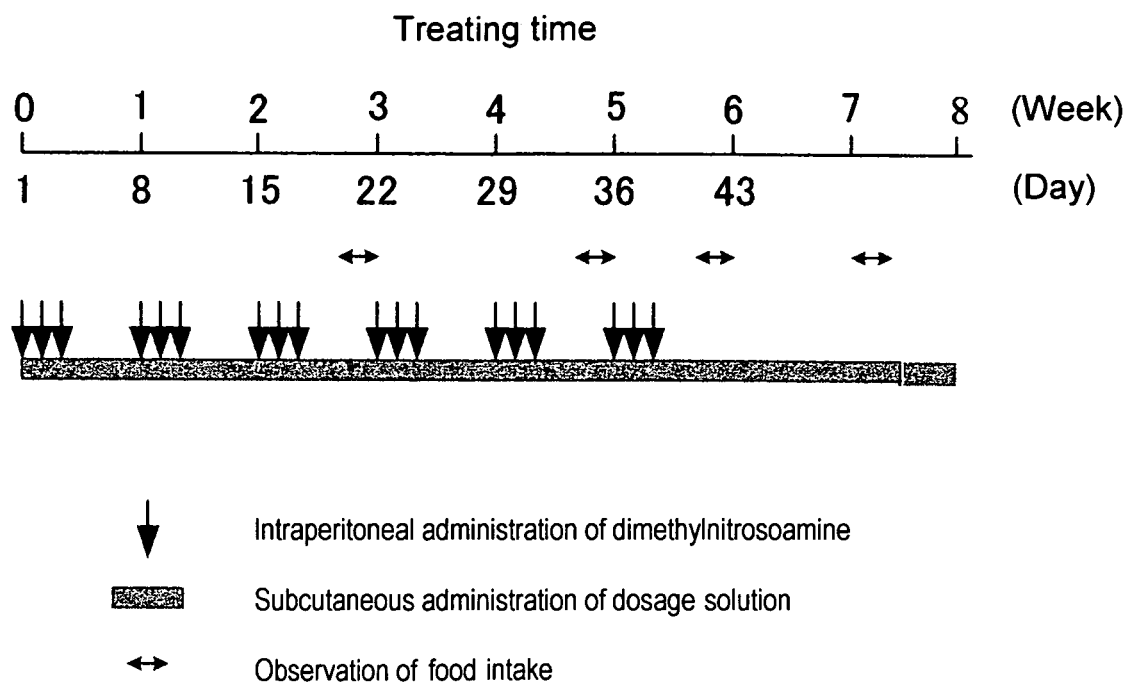
FIG. 1 shows a flowchart of Example 1.

In explanation of the present invention, the following terms are defined as follows:

"Amino acid" is a compound having an amino group and a carboxyl group in the same molecule and, for example, includes all amino acids such as D-form of natural amino acids, β-amino acids, and γ-amino acids in addition to natural amino acids and non-natural amino acids described below.

"Natural amino acid" refers to 20 kinds of amino acids encoded by genes.

"Non-natural amino acid" includes compounds in which the α-carbon atom in α-amino acids is modified. That is, examples of non-natural amino acids include compounds represented by the following formula (6);

(R' and R" may be the same or different, and represent an arbitrary substituent which is not present in natural amino acids, or a hydrogen atom, provided that both of R' and R" are not a hydrogen atom simultaneously). Non-natural amino acids may be of L-form or D-form.

"Alkyl group" means a linear, cyclic, or branched alkyl group, "$C_{1-35}$ alkyl group" means a linear, cyclic or branched alkyl group having 1 to 35 carbon atoms, "$C_{1-20}$ alkyl group" means a linear, cyclic or branched alkyl group having 1 to 20 carbon atoms, and examples of such alkyl groups include methyl, ethyl, proplyl, isopropyl, cyclopropyl, butyl, sec-butyl, isobutyl, tert-butyl, cyclobutyl, pentyl, isopentyl, tert-pentyl, neopentyl, cyclopentyl, 1-methylbutyl, hexyl, isohexyl, cyclohexyl, 3,3-dimethylbutyl, heptyl, cycloheptyl, 1-methylcyclohexyl, 1-proplybutyl, octyl, 1-methylheptyl, nonyl, decyl, undecyl, dodecyl, tridecyl, tetradecyl, pentadecyl, hexadecyl, heptadecyl, octadecyl and nonadecyl. "$C_{1-6}$ alkyl group" means a linear or branched hydrocarbon group having 1 to 6 carbon atoms, such as methyl, ethyl, propyl, isopropyl, butyl, sec-butyl, isobutyl, tert-butyl, pentyl, isopentyl, tert-pentyl, neopentyl, 1-methylbutyl, hexyl, isohexyl and 1-methylpentane, "$C_{1-4}$ alkyl group" means a linear or branched hydrocarbon group having 1 to 4 carbon atoms, such as methyl, ethyl, propyl, isopropyl, butyl, isobutyl, sec-butyl and tert-butyl, "$C_{1-16}$ alkyl group" means a linear or branched hydrocarbon group having 1 to 16 carbon atoms, such as methyl, ethyl, propyl, isopropyl, butyl, sec-butyl, isobutyl, tert-butyl, pentyl, isopentyl, tert-pentyl, neopentyl, 1-methylbutyl, hexyl, isohexyl, 1-methylpentane, 3, 3-dimethylbutyl, heptyl, 1-propylbutyl, octyl, 1-methylheptyl, nonyl, decyl, undecyl, dodecyl, tridecyl, tetradecyl, pentadecyl, and hexadecyl, and "$C_{3-8}$ cycloalkyl group" means a cyclic hydrocarbon group having 3 to 8 carbon atoms, such as cyclopropyl, cyclobutyl, cyclopentyl and cyclohexyl.

"Alkylene group" means a linear or branched alkylene group having 1 to 20 carbon atoms, and examples of the alkylene groups include methylene, ethylene, trimethylene, tetramethylene, pentamethylene, hexamethylene, heptamethylene, octamethylene, decamethylene, dodecamethylene and nonadecamethylene. "$C_{1-6}$ alkylene" means a linear or branched divalent hydrocarbon group having 1 to 6 carbon atoms, such as methylene, ethylene, trimethylene, tetramethylene, pentamethylene and hexamethylene.

"Alkenylene group" means a linear or branched alkenylene group having 2 to 20 carbon atoms, and "$C_{2-6}$ alkenylene" means a linear or branched divalent hydrocarbon group such as vinylene, propenylene, 1-butenylene, 2-butenylene, 1-pentenylene, 2-pentenylene and 3-pentenylene.

"Alkynylene group" means an alkynylene group having 2 to 20 carbon atoms, and "$C_{2-6}$ alkynylene" means a linear or branched divalent hydrocarbon group such as ethynylene, propinylene, 1-butynylene, 2-butynylene, 1-pentynylene, 2-pentynylene and 3-pentynylene.

"Alkenyl group" means a linear or branched alkenyl group having 2 to 20 carbon atoms. Examples of the alkenyl groups include vinyl, allyl, n-propenyl, isopropenyl, n-butenyl, isobutenyl, sec-butenyl, tert-butenyl, n-pentenyl, isopentenyl, neopentenyl, 1-methylpropenyl, n-hexenyl, isohexenyl, 1,1-dimethylbutenyl, 2,2-dimethylbutenyl, 3,3-dimethylbutenyl, 3,3-dimethylpropenyl, 2-ethylbutenyl, heptenyl, octenyl and heptadecenyl.

"Aryl group" means an aromatic carbocyclic ring or ring system include phenyl, 1- or 2-naphthyl, biphenyl, 1-, 2- or 9-anthryl, 1-, 2-, 3-, 4- or 9-phenanthryl, acenaphthyl, anthracenyl and azulenyl.

"Aralkyl group" means a monocyclic aralkyl group having 7 to 16 carbon atoms. Examples of the aralkyl groups include benzyl, p-methoxybenzyl, 3,4-dimethoxybenzyl, o-nitrobenzyl, p-nitrobenzyl, benzhydryl, trityl, methylnaphthyl and ethylphenyl.

As a polypeptide derivative which has an activity of binding to GHS-R and thus elevating intracellular calcium ion concentration and is selected from amino acid sequences represented by SEQ-ID NOS: 1 to 22 in the present invention, a polypeptide derivative containing (i) an amino acid sequence in which 1 or 2 or more [preferably several (not more than 5)] amino acids are deleted at the position other than the first to fourth amino acid residues from the amino-terminus in amino acid sequences represented by SEQ ID NOS:1 to 22, (ii) an amino acid sequence in which 1 or 2 or more [preferably several (not more than 5)] amino acids are added at the position other than the first to fourth positions from the amino-terminus in amino acid sequences represented by SEQ ID NOS:1 to 22, (iii) an amino acid sequence in which 1 or 2 or more [preferably several (not more than)] amino acids other than the first to fourth amino acid residues from the amino-terminus are substituted with other amino acids in amino acid sequences represented by SEQ ID NOS:1 to 22, or (iv) an amino acid sequence having a combination thereof may be used. The amino acid to be added in the (ii), and the amino acid to be substituted in the (iii) may be a non-natural amino acid. It is more preferable that the polypeptide derivative described in the (i) to (iv) have an activity of binding to GHS-R and thus elevating intracellular calcium ion concentration or an activity of inducing secretion of growth hormone through binding to GHS-R.

Alternatively, a peptide in which a partial sequence of amino acids is deleted in preferably amino acid sequences represented by SEQ ID NOS: 1 to 22 may be used. Examples of such peptides include (v) a peptide comprising the first to fourth amino acids from the amino-terminus in amino acid sequences represented by SEQ ID NOS: 1 to 22, (vi) a peptide comprising the first to tenth amino acids from the amino-terminus in amino acid sequences represented by SEQ ID NOS: 1 to 22, and (vii) a peptide comprising the first to fifteenth amino acids from the amino-terminus in amino acid sequences represented by SEQ ID NOS: 1 to 22.

Alternatively, (viii) a peptide comprising an amino acid sequence in which 1 or 2 or more [preferably several (not more than 5)] amino acids are deleted, substituted or added at the amino acid residue(s) other than first to fourth amino acid residues from the amino-terminus as described above in an amino acid sequence comprising the first to tenth amino acids from the amino-terminus of amino acid sequences represented by SEQ ID NOS: 1 to 22, or (iv) a peptide comprising an amino acid sequence in which 1 or 2 or more [preferably several (not more than 5)] amino acids are deleted, substituted or added at the amino acid residue(s) other than the first to fourth amino acid residues from the amino-terminus as described above in an amino acid sequence comprising the first to fifteenth amino acids from the amino-terminus of amino acid sequences represented by SEQ ID NOS:1 to 22 may be used. An amino acid to be added or substituted may be a non-natural amino acid. It is more preferable that a peptide described in the (viii) or (ix) has an activity of binding to GHS-R and thus elevating intracellular calcium ion concentration.

As the polypeptide derivative, there is a preferable embodiment of a polypeptide derivative (hereinafter, referred to as polypeptide derivative I) in which, in amino acid sequences represented by SEQ ID NOS:1 to 22, the second or third amino acid residue from the amino-terminus has a group represented by the following formula (1);

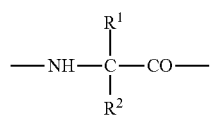

(1)

{wherein $R^1$ and $R^2$ are the same or different, and represent $-T^1-P^1-Q^1$ (wherein $T^1$ represents a divalent hydrocarbon group of a carbon number of 1 to 20, $P^1$ represents —CO—, —$SO_2$—, —CO—O—, —O—CO—, —O—, —CO—S—, —S—CO—, —CS—S—, —S—CS—, —S—, —CO—$NR^4$—, —$NR^4$—CO—, —CO—$NR^4$—CO—, —CS—$NR^4$—CS—, —S—S—, —CS—$NR^4$— or —$NR^4$—CS— ($R^4$ represents a hydrogen atom or a $C_{1-4}$ alkyl group), and $Q^1$ represents a hydrogen atom, an optionally substituted $C_{1-35}$ alkyl group, an optionally substituted $C_{2-35}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ allyl group or an optionally substituted $C_{7-16}$ aralkyl group), $-P^1-Q^1$ (wherein $P^1$ and $Q^1$ are the same defined above) or $-Q^1$ (wherein $Q^1$ is the same as defined above), provided that when one of $R^1$ and $R^2$ is $Q^1$, the other represents $-T^1-P^1-Q^1$ (wherein $T^1$, $P^1$ and $Q^1$ are the same as defined above) or $-P^1-Q^1$ (wherein $P^1$ and $Q^1$ are the same as defined above)}, and which has an activity of binding to GHS-R and thus elevating intracellular calcium ion concentration.

Examples of the "divalent hydrocarbon group" represented by $T^1$ include a divalent hydrocarbon group such as a linear or branched alkylene group having 1 to 20 carbon atoms, preferably 1 to 10 carbon atoms, further preferably 1 to 6 carbon atoms, a linear or branched alkenylene group having 2 to 20 carbon atoms, and a linear or branched alkynylene group having 2 to 20 carbon atoms, a phenylene group and a combination thereof (e.g. $C_{1-6}$ alkylene-phenylene, phenylene-$C_{1-6}$ alkylene, $C_{1-4}$ alkylene-phenylene-$C_{1-4}$ alkylene etc.). Among them, a $C_{1-6}$ alkylene group, a $C_{2-6}$ alkenylene group, a $C_{2-6}$ alkynylene group, a phenylene group, and a $C_{1-4}$ alkylene-phenylene group are preferable. Inter alia, a $C_{1-6}$ alkylene group is preferable.

The "divalent hydrocarbon group" may have a substituent. Examples of the substituents which the "divalent hydrocarbon group" may bear include an optionally substituted $C_{1-6}$ alkyl group [an alkyl group optionally substituted with a hydroxy group, thiol (e.g. mercapto, methylthio, etc.), a $C_{7-16}$ aralkyl group, an optionally substituted $C_{6-14}$ aryl group (e.g. phenyl, naphthyl, hydroxyphenyl, etc.), a heterocycle (e.g. indole, imidazole, etc.), carboxyl, amino, or with guanidino, or an unsubstituted alkyl group], a $C_{7-16}$ aralkyl group, a $C_{6-14}$ aryl group, and an optionally substituted hydroxyl group (e.g. a hydroxy group optionally substituted with a hydrocarbon group; preferably a hydroxy group optionally substituted with a $C_{1-6}$ alkyl group, an unsubstituted hydroxy group), among which an optionally substituted $C_{1-6}$ alkyl group is preferable. The position and the number of substituents are not particularly limited as far as they are chemically acceptable. The number of substituents is preferably about 1 to 4. Examples of the substituents for the "phenylene group" include one to four members selected from a halogen atom (e.g. fluorine, chlorine, bromine, iodine, etc.), a $C_{1-4}$ alkyl group, a $C_{1-4}$ alkoxy group (e.g. methoxy, ethoxy, propoxy, butoxy, etc.), a $C_{1-4}$ alkylthio group, a hydroxy group, a carboxyl group, a cyano group, a nitro group, an amino group, a mono- or di-$C_{1-4}$ alkylamino group, a mercapto group, a $C_{1-4}$ acyl group (e.g. formyl, acetyl, propionyl, butyryl, isobutyryl, etc.), a $C_{2-5}$ alkoxycarbonyl group, a sulfo group (—$SO_3H$), a $C_{1-4}$ alkylsulfonyl group, a carbamoyl group and a mono- or di-$C_{2-5}$ alkylcarbamoyl group (e.g. N-methylcarbamoyl, N-ethylcarbamoyl, N,N-dimethylcarbamoyl, N,N-diethylcarbamoyl, etc.).

As a group represented by $P^1$, —CO—O—, —O—CO—, —O—, —S—, —S—S—, —CO—$NR^4$— or —$NR^4$—CO— ($R^4$ represents a hydrogen atom or a $C_{1-4}$ alkyl group) is preferable, and —O—CO— is particularly preferable.

As the "alkyl group" represented by $Q^1$, a $C_{1-20}$ linear or branched alkyl group is preferable. More preferably, a $C_{1-16}$ linear or branched alkyl group is preferable and, inter alia, a $C_7$ alkyl group is preferable.

As the "alkenyl group" represented by $Q^1$, a $C_{2-20}$ linear or branched alkenyl group is preferable.

Examples of the substituents which the "alkyl group" or the "alkenyl group" represented by $Q^1$ may bear include a halogen atom; a carboxy group; a hydroxy group; an amino group; a nitro group; a cyano group; a $C_{1-6}$ alkoxy group such as methoxy, ethoxy, propoxy, butoxy, pentyloxy, and hexyloxy; a $C_{7-16}$ aralkyloxy group such as formyloxy, acetoxy, and propionyloxy; a $C_{2-7}$ alkoxycarbonyl group such as methoxycarbonyl, ethoxycarbonyl, and propoxycarbonyl; a $C_{6-14}$ aryl group; a $C_{1-6}$ alkylthio group such as methylthio, ethylthio, propylthio, butylthio, and isobutylthio; a $C_{1-6}$ alkylsulfinyl group such as methylsulfinyl, and ethylsulfinyl; a $C_{1-6}$ alkylsulfonyl group such as methylsulfonyl, and ethylsulfonyl; a $C_{1-6}$ alkylamino group such as methylamino, ethylamino, propylamino, and butylamino; an acylamino group such as acetamide, and propionylamide. The number of the substituents is about 1 to 5, preferably about 1 to 3.

Examples of the substituents in the optionally substituted "cycloalkyl group", "aryl group" or "aralkyl group" represented by $Q^1$ include a $C_{1-6}$ alkyl group; a hydroxy group; a $C_{1-6}$ alkoxy group such as methoxy, ethoxy, propoxy, isopropoxy, buthoxy, pentyloxy, and hexyloxy; a halogen atom such as fluorine, chlorine, and bromine; a nitro group; a cyano group; a $C_{1-6}$ acyl group; a $C_{1-6}$ acyloxy group such as formyloxy, acetoxy, and propionyloxy; a mercapto group; a $C_{1-6}$ alkylthio group such as methylthio, ethylthio, propylthio, butylthio, and isobutylthio; an amino group; a $C_{1-6}$ alkylamino group such as methylamino, ethylamino, propylamino, and butylamino; a di-$C_{1-6}$ alkylamino group such as dimethylamino, diethylamino, dipropylamino, and dibutylamino; a carboxy group; a $C_{2-7}$ alkoxycarbonyl group such as methoxycarbonyl, ethoxycarbonyl, and propoxycarbonyl; an amido group; a halogenated alkyl group such as trifluoromethyl; a $C_{1-6}$ alkylsulfonyl group such as methylsulfonyl, and ethylsulfonyl; an aminosulfonyl group; a $C_{3-7}$ cycloalkyl group; an acylamide group such as acetamide, and propionylamide. The position and the number of the substituents are not particularly limited as far as they are within a chemically acceptable range. The number of the substituents is preferably about 1 to 3.

The "$C_{1-6}$ alkylene-$C_{3-8}$ cycloalkyl group" represented by $Q^1$ is a substituent in which the alkyl group of 1 to 6 carbon atoms and the cycloalkyl group of 3 to 8 carbon atoms are linked together. Preferable is a $C_{1-4}$ alkylene-phenylene. The substituent in the "optionally substituted $C_{1-6}$ alkylene-$C_{3-8}$ cycloalkyl group" may be located in the $C_{1-6}$ alkyl group moiety, or $C_{1-8}$ cycloalkyl group moiety. Examples of the substituent in the $C_{1-6}$ alkyl group moiety include the same substituents as substituents of the alkyl group, and examples of the substituent in the $C_{3-8}$ cycloalkyl group moiety include the same substituents as substituents of the cycloalkyl group.

In the polypeptide derivative I of the aforementioned embodiment, it is more preferable that the second or third amino acid residue from the amino-terminus has a group represented by the following formula (2);

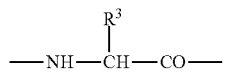
(2)

{wherein $R^3$ represents $-T^2-P^2-Q^2$ (wherein $T^2$ represents a $C_{1-6}$ alkylene group, a $C_{2-6}$ alkenylene group, or a $C_{1-4}$ alkylene-phenylene group, $P^2$ represents —CO—O—, —O—CO—, —O—, —S—, —S—S—, —CO—NR$^4$— or —NR$^4$—CO— (R$^4$ represents a hydrogen atom or a $C_{1-4}$ alkyl group), and $Q^2$ represents an optionally substituted $C_{1-20}$ alkyl group, an optionally substituted $C_{2-20}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group) or $P^2$-$Q^2$ (wherein $P^2$ and $Q^2$ are the same as defined above)}.

When the substituent $R^3$ is $-T^2-P^2-Q^2$ in the formula (2), the substituent $T^2$ is preferably a $C_{1-6}$ alkylene group or a $C_{1-4}$ alkylene-phenylene group, and more preferably methylene, ethylene, propylene, butylene or methylene-phenylene.

When the substituent $R^3$ is $-T^2-P^2-Q^2$ or $-P^2Q^2$ in the formula (2), it is preferable that the substituent $P^2$ is —CO—O—, —O—CO—, —S—S—, —CO—NR$^4$— or —NR$^4$—CO— (R$^4$ represents a hydrogen atom or a $C_{1-4}$ alkyl group), and the substituent $Q^2$ is an optionally substituted $C_{1-20}$ alkyl group (preferably a $C_{1-16}$ alkyl group, particularly preferably, a $C_7$ alkyl group) or an optionally substituted $C_{2-20}$ alkenyl group, or the substituent $P^2$ is —O— or —S—, and the substituent $Q^2$ is an optionally substituted $C_{1-20}$ alkyl group, an optionally substituted $C_{2-20}$ alkenyl group, an optionally substituted $C_{3-8}$ cycloalkyl group, an optionally substituted $C_{1-6}$ alkylene-$C_{3-8}$ cycloalkyl group, an optionally substituted $C_{6-14}$ aryl group or an optionally substituted $C_{7-16}$ aralkyl group. The substituent in the group represented by $Q^2$ is the same as the substituent in the group represented by $Q^1$.

As an amino acid residue which is second or third from the amino-terminus in the polypeptide derivative I of the aforementioned embodiment, the following amino acid residues are also preferable. First, examples of such amino acids include amino acid residues in which the hydroxy group of an amino acid residue having a hydroxy group in the side chain forms ester, thioester or ether. Specifically, examples of such amino acids include serine, threonine, tyrosine and oxyproline in which the hydroxy group in the side chain is converted into a substituent represented by —OCO-Q$^2$, —OCS-Q$^2$ or —O-Q$^2$ (Q$^2$ is the same as defined above). Secondly, examples of such amino acids include amino acid residues in which the mercapto group of an amino acid residue having a mercapto group in the side chain forms thioester, thioether or disulfide. Specifically, example of such amino acids include cysteine in which the mercapto group is converted into a substituent represented by —SCO-Q$^2$, —SCS-Q$^2$, S-Q$^2$ or —S—S-Q$^2$ (Q$^2$ is the same as defined above). Then, examples of such amino acids include amino acid residues in which the amino group in the side chain of an amino acid residue having an amino group in the side chain forms alkylamino, dialkylamino, amido, or carbamoyl. Specifically, examples of such amino acids include lysine and arginine in which an amino group in the side chain is converted into a substituent represented by —NR$^4$—CO-Q$^2$, —NR$^4$—CS-Q$^2$, —NH(Q$^2$), —N(Q$^2$)(Q$^{2'}$), —NR$^4$—CO—NR$^4$-Q$^2$, —NR$^4$—CS—NR$^4$-Q$^2$ (Q$^2$ and R$^4$ are the same defined above, Q$^{2'}$, may be the same as or different from Q$^2$, and has the same meaning as that of Q$^2$). Then, examples of such amino acids include amino acid residues in which the imino group of an amino acid residue having an imino group in the side chain forms alkylamino, dialkylamino, amido, or carbamoyl. Specifically, examples of such amino acids histidine, tryptophan, proline and oxyproline in which the imino group in the side chain is converted into a substituent represented by the following formula;

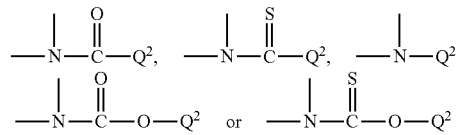

(wherein Q$^2$ is the same as defined above).

It is more preferable that an amino acid residue which is second or third from the amino-terminus is serine, threonine, tyrosine or oxyproline in which the hydroxy group in the side chain is converted, inter alia, into a substituent represented by —OCO-Q$^2$, —OCS-Q$^2$ or O-Q$^2$ (Q$^2$ is as defined above), or cysteine in which a mercapto group on a side chain is converted into a substituent represented by —SCO-Q$^2$, —SCS-Q$^2$, —S-Q$^2$ or —S—S-Q$^2$ (Q$^2$ is the same as defined above). It is further preferable that an amino acid residue which is second or third from the amino-terminus is serine in which the hydroxy group in the side chain is converted into a substituent represented by —OCO-Q$^2$, —OCS-Q$^2$ or —O-Q$^2$ (Q$^2$ is the same as defined above), or cystine in which the mercapto group in the side chain is converted into a substituent represented by —SCO-Q$^2$ (Q$^2$ is the same as defined above). It is particularly preferable that an amino acid residue which is second or third from the amino-terminus is converted into a substituent represented by —OCO-Q$^2$ (Q$^2$ is the same as defined above).

As an amino acid residue which is second or third from the amino-terminus, there is preferably exemplified an amino acid residue in which fatty acid is linked to the hydroxy group of the side chain via ester bond. In this case, examples of amino acids having a hydroxy group in the side chain include serine, threonine, tyrosine and oxyproline, inter alia, serine or threonine is preferable, and serine is particularly preferable. The fatty acids may be substituted or unsubstituted, and the number of carbon atoms thereof is preferably 2 to 36, more preferably 2 to 21, further preferably 2 to 17. Specifically, examples of such fatty acids include saturated fatty acids such as acetic acid, butyric acid, isobutyric acid, valeric acid (pentanoic acid), isovaleric acid, pivalic acid, caproic acid (hexanoic acid), octanoic acid (preferably caprylic acid), decanoic acid (preferably capric acid), dodecanoic acid (preferably lauric acid), myristic acid, palmitic acid, stearic acid, arachidic acid, and ligroceric acid, and unsaturated fatty acids such as sorbic acid, oleic acid, linoleic acid, linolenic acid, ricinoleic acid, arachidonic acid, eicosapentaenoic acid (EPA) and docosahexaenoic acid (BHA). Among them, acetic acid, lactic acid, caproic acid (hexanoic acid), and octanoic acid (preferably caprylic acid) are preferable. Among them, octanoic acid is especially preferable.

Preferable examples of the polypeptide derivative I include a polypeptide derivative in which serine, threonine or leucine at the second or third position from the amino-terminus of amino acid sequences represented by SEQ ID NOS: 1 to 22 has the aforementioned formula (1), in human ghrelin or amino acid sequences represented by SEQ ID NOS: 1 to 22 constituting the ghrelin, and which has an activity of binding to GHS-R and thus elevating intracellular calcium ion concentration.

In addition, the polypeptide derivative I may be a polypeptide derivative having an amino acid sequence in which, in the amino acid sequences represented by SEQ ID NOS: 1 to 22 constituting the human ghrelin, 1 or 2 or more [preferably several (2 to 5)] amino acids are deleted, added or substituted at the amino acid residues other than the first to fourth amino acid residues from the amino-terminus in the amino acid sequences represented by SEQ ID NOS: 1 to 22, or an amino acid sequence comprising a combination thereof, and the second or third amino acid residue from the amino-terminus has the aforementioned formula (1), and which has an activity of binding to GHS-R and thus elevating intracellular calcium ion concentration. In the foregoing, an amino acid to be added or/and an amino acid to be substituted may be a non-natural amino acid. In addition, in the present invention, in an amino acid sequence selected from amino acid sequences represented by SEQ ID NOS:1 to 22 constituting the human ghrelin, there can also be preferably used (a) a polypeptide derivative having an amino acid sequence of the first to fourth amino acids from the amino-terminus in amino acid sequences represented by SEQ ID NOS: 1 to 22, in which the second or third amino acid from the amino-terminus has the aforementioned formula (1), and which has an activity of binding to GHS-R and thus elevating intracellular calcium ion concentration, (b) a polypeptide derivative having an amino acid sequence of the first to tenth amino acids from the amino-terminus in amino acid sequences represented by SEQ ID NOS: 1 to 22, in which the second or third amino acid from the amino-terminus has the aforementioned formula (1), and which has an activity of binding to GHS-R and thus elevating intracellular calcium ion concentration, or (c) a polypeptide derivative having an amino acid sequence of the first to fifteenth amino acids from the amino-terminus in amino acid sequences represented by SEQ ID NOS: 1 to 22, in which the second or third amino acid from the amino-terminus has the aforementioned formula (1), and which has an activity of binding to GHS-R and thus elevating intracellular calcium ion concentration.

In addition, in an amino acid sequence selected from amino acid sequences represented by SEQ ID NOS: 1 to 22, there can be preferably used (d) a polypeptide derivative having an amino acid sequence in which 1 or 2 or more [preferably several (2 to 5)] amino acids are deleted, substituted or added at the amino acid residue(s) other than the first to fourth amino acid residues from the amino-terminus as described above in an amino acid sequence of the first to tenth amino acids from the amino-terminus, and the second or third amino acid from the amino-terminus has the aforementioned formula (1), and which has an activity of binding to GHS-R and thus elevating intracellular calcium ion concentration, or (e) a polypeptide derivative having an amino acid sequence in which 1 or 2 or more [preferably several (2 to 5)] amino acids are deleted, substituted or added at the amino acid residue(s) other than the first to fourth amino acid residues from the amino-terminus as described above in an amino acid sequence comprising the first to fifteenth amino acids from the amino-terminus, and the second or third amino acid from the amino-terminus has the aforementioned formula (1), and which has an activity of binding to GHS-R and thus elevating intracellular calcium ion concentration. An amino acid to be added or an amino acid to be substituted may be a non-natural amino acid.

In addition, in the present invention, a polypeptide derivative (hereinafter referred to as polypeptide derivative II) which is represented by the formula (3); X—Y—Z (wherein X represents an organic group having a molecular chain length corresponding to an amino acid residue, a dipeptide or a tripeptide, and comprising one or more kinds of atoms selected from the group consisting of C, H, O, N and S, Y represents a group represented by the following formula (1);

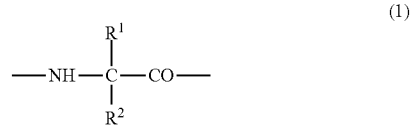

{wherein $R^1$ and $R^2$ are the same or different, and represent $-T^1-P^1-Q^1$ (wherein $T^1$, $P^1$ and $Q^1$ are the same as defined above), $-P^1-Q^1$ (wherein $P^1$ and $Q^1$ are the same as defined above) or $-Q^1$ (wherein $Q^1$ is the same as defined above), Z represents a natural amino residue or an optical isomer thereof, and $Q^1$ is the same as defined above}, and which has an activity of binding to GHS-R and thus elevating intracellular calcium ion concentration.

In X of the aforementioned formula (3), the molecular chain length corresponding an amino acid residue refers to an organic group having a molecular chain length corresponding to a total length of N—C bond and C—C bond which is a peptide unit of one amino acid residue represented by the formula;

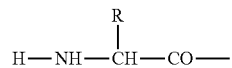

(R represents a side chain linked to an ax carbon atom of a natural amino acid). The molecular chain length refers to a length containing a variation of about ±20%, preferably about ±10%, depending on the binding format of atoms C, O, N and S constituting a molecular chain length.

The molecular chain length corresponding to a dipeptide refers to a molecular chain length corresponding to a peptide unit of two molecules of an amino acid residue represented by the formula;

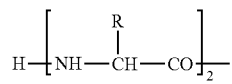

(R is the same as defined above, and R may be the same or different every repetition unit), and the length containing a variation of about ±20%, preferably about ±10% depending on the binding format of atoms C, O, N and S constituting the chain length. The molecular chain length corresponding to a tripeptide refers to a molecular chain length corresponding to a peptide unit of three molecules of an amino acid residue represented by the formula:

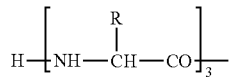

(R is the same as defined above, and R may be the same or different every repetition unit), and the length containing a variation of about ±20%, preferably about ±10% depending on the binding format of atoms C, O, N and S constituting the chain length. Inter alia, it is preferable that X has a molecular chain length corresponding to an amino acid residue or a dipeptide, and it is more preferable that X has a molecular chain length corresponding to a dipeptide.

It is particularly preferable that X is an organic group represented by the formula (4); $H_2N-X^1-CO-$ ($X^1$ represents a $C_4$ alkylene group optionally having a substituent, or an organic group in which at least one carbon atom of the $C_4$ alkylene group is substituted with O, N or S). Examples of $X^1$ include a substituent represented by $-(C(R^5)(R^6))_4-$ (wherein $R^5$ and $R^6$ may be the same or different, and represent an optionally substituted $C_{1-6}$ alkyl group or an optionally substituted $C_{2-6}$ alkenyl group, and $R^5$ and $R^6$ may be the same or different every repetition unit), and a substituent in which, among four repetition units in the aforementioned substituent, at least one unit is substituted with ($NR^7$) (wherein $R^7$ represents an optionally substituted $C_{1-6}$ alkyl group or an optionally substituted $C_{2-6}$ alkenyl group) or O. Specifically, examples of $X^1$ include $-(CH_2)_3CH(CH_2OH)-$, $-(CH_2)_4-$, $-C(CH_3)_2-(CH_2)_3-$ or $-CH(CH_3)-(CH_2)_2-CH(CH_3)-$, $-CH_2-CH_2-O-CH_2-$, $-CH_2-CH_2-S-CH_2-$, $-CH_2-N(CH_3)-CH_2-CH_2-$, $-CH_2-O-CH(CH_2OH)-CH_2-$.

In the aforementioned formula (3), examples of Y include the same examples as groups represented by the formula (1) which the second or third amino acid from the amino-terminus of the polypeptide derivative I bears.

In the aforementioned formula (3), Z is not particularly limited as far as it is a natural amino acid residue or an optical isomer thereof, but a hydrophobic natural amino acid or a D-form thereof is preferable. Examples of the hydrophobic natural amino acids include leucine, valine, isoleucine, tryptophan and phenylalanine and, inter alia, an aromatic hydrophobic amino acid such as tryptophan and phenylalanine is preferable. In addition, a basic natural amino acid such as lysine, arginine and histidine is also preferable and, inter alia, lysine is more preferable as Z.

In addition, there is also exemplified, as other preferable embodiment, a polypeptide derivative having a structure in which a partial amino acid sequence corresponding to an amino acid sequence of the fifth amino acid from the amino-terminus to the carboxyl-terminus in one amino acid sequence selected from the group consisting of amino acid sequences represented by SEQ ID NOS: 1 to 22, or an amino acid sequence in which 1 or 2 or more [preferably several (2 to 5)] amino acids are deleted, substituted or added in the partial amino acid sequence is bound to a peptide-type compound consisting of a structure represented by the formula (3); X—Y—Z (wherein X, Y and Z are the same as defined above) (hereinafter, referred to as a polypeptide derivative III).

In the polypeptide derivative III, the description regarding the polypeptide derivative II is also used for a polypeptide derivative consisting of a structure represented by the formula (3); X—Y—Z (wherein X, Y and Z are the same as defined above).

In the polypeptide derivative III, as an amino acid sequence which is bound to a polypeptide derivative consisting of a structure represented by the formula (3); X—Y—Z (wherein X, Y and Z are the same as defined above), there is preferably exemplified a partial amino acid sequence corresponding to an amino acid sequence of the fifth to tenth amino acids from the amino-terminus of one amino acid sequence selected from the group consisting of amino acid sequences represented by SEQ ID NOS: 1 to 22, or an amino acid sequence in which one or two or more [preferably several (2 to 5)] amino acids are deleted, substituted or added in the said partial amino acid sequence; or a partial amino acid sequence corresponding to an amino acid sequence of the fifth to fifteenth amino acids from the amino-terminus in one amino acid sequence selected from the group consisting of amino acid sequences represented by SEQ ID NOS: 1 to 22, or an amino acid sequence in which one or two or more [preferably several (2 to 5)] amino acids are deleted, substituted or added in the said partial amino acid sequence.

In addition, in the present invention, a polypeptide derivative (hereinafter, referred to as polypeptide derivative IV) consisting of a structure represented by the formula (5); A-B-C-D [wherein A and D are a natural amino acid residue or an optical isomer thereof, one or both of B and C represent(s) a group represented by the following formula (1);

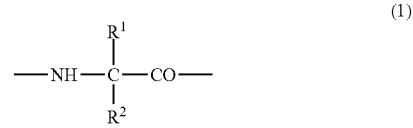

(wherein $R^1$ and $R^2$ are the same as defined above),
when only one of B and C is an amino acid residue represented by the formula (1), the other is a natural amino acid residue or an optical isomer thereof] can also be preferably used.

In the aforementioned formula (5), when B or C is a group represented by the formula (1), examples of such group include the same groups as those of the second or third amino acid residue from the amino terminus in the polypeptide derivative I. In the case where only C is a group represented by the formula (1), B may be a natural amino residue or an optical isomer thereof, inter alia, preferably alanine, serine, or histidine having a small side chain, or a D-form thereof, or glycine. When only B is a group represented by the formula (1), C may be a natural amino acid residue or an optical isomer thereof and, inter alia, a hydrophobic natural amino acid or a basic natural amino acid, or a D-form thereof is preferable.

In the aforementioned formula (5), A may be a natural amino acid residue or an optical isomer thereof and, inter alia, glycine is preferable.

In the aforementioned formula (5), D may be a natural amino acid residue or an optical isomer thereof and, inter alia, a hydrophobic natural amino aid, or a basic natural amino acid, or a D-form thereof is preferable.

In the present invention, there are exemplified, as other preferable embodiment, a polypeptide derivative (hereinafter, refereed to as polypeptide derivative V) consisting of a structure in which a partial amino acid sequence corresponding to an amino acid sequence of from the fifth amino acid from the amino-terminus to the carboxyl-terminus in one amino acid sequence selected from the group consisting of amino acid sequences represented by SEQ ID NOS: 1 to 22, and an amino acid sequence in which one or two or more [preferably several (2 to 5)] amino acids are deleted, substituted or added in the said partial amino acid sequence is bound to a polypeptide derivative consisting of a structure represented by the formula (5); A-B-C-D (wherein A, B, C and D are the same as defined above).

In the polypeptide derivative V, the description regarding the polypeptide derivative IV can also be used for the polypeptide derivative consisting of a structure represented by the formula (5); A-B-C-D (wherein A, B, C and D are the same as defined above).

In the polypeptide derivative V, as an amino acid sequence which is bound to a polypeptide derivative consisting of a structure represented by the formula (5); A-B-C-D (wherein A, B, C and D are the same as defined above), there are preferably exemplified a partial amino acid sequence corresponding to an amino acid sequence of the fifth to tenth amino acids from the amino-terminus in one amino acid sequence selected from the group consisting of amino acid sequences represented by SEQ ID NOS: 1 to 22, and an amino acid sequence in which one or two or more [preferably several (2 to 5)] amino acids are deleted, substituted or added in the said partial amino acid sequence; or a partial amino acid sequence of the fifth to fifteenth amino acids from the amino-terminus, and an amino acid sequence in which one or two or more [preferably several (2 to 5)] amino acids are deleted, substituted or added in the said partial amino acid sequence In the aforementioned ghrelin or polypeptide derivatives I to V, a basic amino acid may be further bound to the carboxyl-terminus. Herein, examples of the basic amino acid include basic natural amino acids such as the aforementioned lysine, arginine and histidine, or D-form thereof, or D- or L-N-methylamino acid thereof. In addition, in the aforementioned ghrelin or polypeptide derivatives I to V, the carboxyl group at the carboxyl-terminus may form a salt, ester or amide. When a carboxyl group forms a salt, the salt is preferably a pharmaceutically acceptable salt. Examples of the pharmaceutically acceptable salts include salts with an inorganic base, salts with an organic base, salts with an inorganic acid, salts with an organic acid, and salts with a basic or acidic amino acid. Preferable examples of salts with an inorganic base include alkali metal salts such as a sodium salt, and a potassium salt; alkaline earth metal salts such as a calcium salt, and a magnesium salt; and an aluminum salt, and an ammonium salt. Preferable examples of salts with an organic base include salts with trimethylamine, triethylamine, pyridine, picoline, ethanolamine, diethanolamine, triethanolamine, dicyclohexylamine, and N,N'-dibenzylethylenediamine. Preferable examples of salts with an inorganic acid include salts with hydrochloric acid, hydrobromic acid, nitric acid, sulfuric acid, and phosphoric acid. Preferable examples of salts with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Preferable examples of salts with a basic amino acid include salts with argine, lysine, and ornithine, and preferable examples of salts with an acidic amino acid include salts with aspartic acid, and glutamic acid. Among these salts, an acetic acid salt, a sodium salt, and a potassium salt are most preferable.

When the carboxyl group at the carboxyl-terminus forms an ester, examples of such esters include esters represented by the formula; $COOR^8$ (wherein $R^8$ represents a $C_{1-6}$ alkyl group, a $C_{2-6}$ alkenyl group, a $C_{6-14}$ aryl group, or a $C_{7-16}$ aralkyl group).

When the carboxyl group at the carboxyl-terminus forms an amide, examples of such amides include amides represented by the formula; $—CON(R^9)(R^{10})$ ($R^9$ and $R^{10}$ are the same or different, and represent a hydrogen atom, a $C_{1-6}$ alkyl group, a $C_{2-6}$ alkenyl group, a $C_{6-14}$ aryl group, or a $C_{7-16}$ aralkyl group). Inter alia, $—CONH_2$ is preferable.

When the carboxyl group at the carboxyl-terminus forms an ester or amide, a basic group such as an amino group or a guanidido group may be further bound to the ester or amide.

As an embodiment of the polypeptide derivative which can be used in the present invention, there are preferably exemplified:

ghrelin derived from human (a polypeptide derivative wherein the third serine residue of an amino acid sequence represented by SEQ ID NO: 1 or 2 is acylated with acetic acid, butyric acid, valeric acid, octanoic acid or decanoic acid);

ghrelin derived from rat (a polypeptide derivative wherein the third serine residue of an amino acid sequence represented by SEQ ID NO:3 or 4 is acylated with acetic acid, butyric acid, valeric acid, octanoic acid or decanoic acid);

ghrelin derived from mouse (a polypeptide derivative wherein the third serine residue of an amino acid sequence represented by SEQ ID NO: 5 is acylated with octanoic acid or decanoic acid);

ghrelin derived from pig (a polypeptide derivative wherein the third serine residue of an amino acid sequence represented by SEQ ID NO: 6 or 7 is acylated with octanoic acid or decanoic acid);

ghrelin derived from cow (a polypeptide derivative wherein the third serine residue of an amino acid sequence represented by SEQ ID NO: 8 is acylated with octanoic acid or decanoic acid);

ghrelin derived from pig (a polypeptide derivative wherein the third serine residue of an amino acid sequence represented by SEQ ID NO: 7 is acylated with octanoic acid or decanoic acid);

ghrelin derived from dog (a polypeptide derivative wherein the third serine residue of an amino acid sequence represented by SEQ ID NO: 10 is acylated with octanoic acid or decanoic acid);

ghrelin derived from eel (a polypeptide derivative wherein the third serine residue of an amino acid sequence represented by SEQ ID NO: 11 is acylated with octanoic acid or decanoic acid);

ghrelin derived from rainbow trout (a polypeptide derivative wherein the third serine residue of an amino acid sequence represented by SEQ ID NO: 12 or 13 is acylated with octanoic acid or decanoic acid);

ghrelin derived from chicken (a polypeptide derivative wherein the third serine residue of an amino acid sequence represented by SEQ ID NO: 14, 15 or 16 is acylated with octanoic acid or decanoic acid);

ghrelin derived from frog (a polypeptide derivative wherein the third serine residue of an amino acid sequence represented by SEQ ID NO: 17 or 18 is acylated with octanoic acid or decanoic acid);

ghrelin derived from tilapia (a polypeptide derivative wherein the third serine residue of an amino acid sequence represented by SEQ ID NO: 19 is acylated with octanoic acid or decanoic acid);

ghrelin derived from catfish (a polypeptide derivative wherein the third serine residue of an amino acid sequence represented by SEQ ID NO: 20 or 21 is acylated with octanoic acid or decanoic acid); and ghrelin derived from horse (a polypeptide derivative wherein the third serine residue of an amino acid sequence represented by SEQ ID NO: 22 is acylated with octanoic acid or decanoic acid).

Ghrelin derived from human, rat, mouse, pig, cow, sheep, dog or horse is more preferable, and ghrelin derived from human is particularly preferable.

In addition, there are preferably used:

Ghrelin(1-9)-amide: H-Gly-Ser-Ser(CO—$C_7H_{15}$)-Phe-Leu-Ser-Pro-Glu-His-$NH_2$ (SEQ ID NO:23);

[Ser$^3$(Acetyl)]-rGhrelin: GSS(CO—$CH_3$)FLSPE-HQKAQQRKESKKPPAKLQPR (SEQ ID NO:24)

[Ser$^3$(Butyryl)]-rGhrelin: GSS(CO—$C_3H_7$)FLSPE-HQKAQQRKESKKPPAKLQPR (SEQ ID NO:25)

[Ser$^3$(Hexanoyl)]-rGhrelin: GSS(CO—$C_5H_{11}$)FLSPE-HQKAQQRKESKKPPAKLQPR (SEQ ID NO:26);

[Ser$^3$(Decanoyl)]-rGhrelin: GSS(CO—$C_9H_{19}$)FLSPE-HQKAQQRKESKKPPAKLQPR (SEQ ID NO:27)

[Ser$^3$(Lauroyl)]-rGhrelin: GSS(CO—$C_{11}H_{23}$)FLSPE-HQKAQQRKESKKPPAKLQPR (SEQ ID NO:28);

[Ser$^3$(Palmitoyl)]-rGhrelin: GSS(CO—$C_{15}H_{31}$)FLSPE-HQKAQQRKESKKPPAKLQPR (SEQ ID NO:29);

[Ser$^3$(3-Phenylpropionyl)]-hGhrelin: GSS(CO—$CH_2CH_2Ph$)FLSPEHQRVQQRKESKKPPAKLQPR (SEQ ID NO:30);

[Ser$^3$(3-Octenoyl)]-hGhrelin: GSS(CO—$CH_2CH=CH(CH_2)_3CH_3$)FLSPEHQRVQQRKESKKPPAKLQPR (SEQ ID NO:31);

[Ser$^3$ (Octyl)]-hGhrelin: GSS($C_8H_{17}$) FLSPE-HQRVQQRKESKKPPAKLQPR (SEQ ID NO:32);

[Cys$^3$(Octyl)]-rGhrelin: GSC($C_8H_{17}$) FLSPE-HQKAQQRKESKKPPAKLQPR (SEQ ID NO:33)

hGhrelin(1-15): H-Gly-Ser-Ser(CO—$C_7H_{15}$)-Phe-Leu-Ser-Pro-Glu-His-Gln-Arg-Val-Gln-Gln-Arg-OH (SEQ ID NO:34);

[des Gln$^{14}$]-rGhrerin: GSS(CO—$C_7H_{15}$)FLSPE-HQKAQRKESKKPPAKLQPR (SEQ ID NO:35);

hGhrelin(1-11): H-Gly-Ser-Ser(CO—$C_7H_{15}$)-Phe-Leu-Ser-Pro-Glu-His-Gln-Arg-OH (SEQ ID NO:36);

Ghrelin(1-10): H-Gly-Ser-Ser(CO—$C_7H_{15}$)-Phe-Leu-Ser-Pro-Glu-His-Gln-OH (SEQ ID NO:37);

Ghrelin(1-8)-amide: H-Gly-Ser-Ser(CO—$C_7H_{15}$)-Phe-Leu-Ser-Pro-Glu-$NH_2$ (SEQ ID NO:38);

Ghrelin(1-7)-amide: H-Gly-Ser-Ser(CO—$C_7H_{15}$)-Phe-Leu-Ser-Pro-$NH_2$ (SEQ ID NO:39);

Ghrelin(1-6)-amide: H-Gly-Ser-Ser(CO—$C_7H_{15}$)-Phe-Leu-Ser-$NH_2$ (SEQ ID NO:40);

Ghrelin(1-5): H-Gly-Ser-Ser(CO—$C_7H_{15}$)-Phe-Leu-OH (SEQ ID NO:41);

Ghrelin(1-5)-amide: H-Gly-Ser-Ser(CO—$C_7CH_{15}$)-Phe-Leu-$NH_2$ (SEQ ID NO:42);

Ghrelin(1-4)-amide: H-Gly-Ser-Ser(CO—$C_7H_{15}$)-Phe-$NH_2$ (SEQ ID NO:43);

[Lys$^8$]-Ghrelin(1-8)-amide: H-Gly-Ser-Ser(CO—$C_7H_{15}$)-Phe-Leu-Ser-Pro-Lys-$NH_2$ (SEQ ID NO:44);

[Arg$^8$]-Ghrelin(1-8)-amide: H-Gly-Ser-Ser(CO—$C_7H_{15}$)-Phe-Leu-Ser-Pro-Arg-$NH_2$ (SEQ ID NO:45);

[Lys$^6$]-Ghrelin(1-6)-amide: H-Gly-Ser-Ser(CO—$C_7H_{15}$)-Phe-Leu-Lys-$NH_2$ (SEQ ID NO:46);

[Lys$^5$]-Ghrelin(1-5)-amide: H-Gly-Ser-Ser(CO—$C_7H_{15}$)-Phe-Lys-$NH_2$ (SEQ ID NO:47);

[N-Aminopentanoyl]-Ghrelin(3-7)-amide: $NH—(CH)_4$—CO-Ser(CO—$C_7H_{15}$)-Phe-Leu-Ser-Pro-$NH_2$ (SEQ ID NO:48);

[Leu$^2$]-Ghrelin(1-7)-amide: H-Gly-Leu-Ser(CO—$C_7H_{15}$)-Phe-Leu-Ser-Pro-$NH_2$ (SEQ ID NO:49);

[His$^2$]-Ghrelin(1-7)-amide: H-Gly-His-Ser(CO—$C_7H_{15}$)-Phe-Leu-Ser-Pro-$NH_2$ (SEQ ID NO:50);

[Lys$^2$]-Ghrelin(1-7)-amide: H-Gly-Lys-Ser(CO—$C_7H_{15}$)-Phe-Leu-Ser-Pro-$NH_2$ (SEQ ID NO:51);

[Cys$^3$(Octyl)]-Ghrelin(1-7)-amide: H-Gly-Ser-Cys($C_8H_{17}$)-Phe-Leu-Ser-Pro-$NH_2$ (SEQ ID NO:52);

[Ser$^3$(Octyl)]-Ghrelin(1-7)-amide: H-Gly-Ser-Ser($C_8H_{17}$)-Phe-Leu-Ser-Pro-$NH_2$ (SEQ ID NO:53);

[Asp$^3$(O-Heptyl)]-hGhrelin: GSD(O—$C_7H_{15}$)FLSPE-HQRVQQRKESKKPPAKLQPR (SEQ ID NO:54);

[Asp$^3$(NH-Heptyl)]-hGhrelin: GSD(NH—$C_7H_{15}$)FLSPE-HQRVQQRKESKKPPAKLQPR (SEQ ID NO:55);

[Dap$^3$(Octanoyl)]-hGhrelin: GS-NH-$^L$CH($CH_2NHCO$—$C_7H_{15}$)—CO-FLSPEHQRVQQRKESKKPPAKLQPR (SEQ ID NO:56);

[Cys$^3$(S-Heptyl)]-hGhrelin: GSC(S—$C_7H_{15}$)FLSPE-HQRVQQRKESKKPPAKLQPR (SEQ ID NO:57);

[Adod$^3$]-hGhrelin: GS-NH—CH(n-$C_{10}H_{21}$)—CO-FLSPE-HQRVQQRKESKKPPAKLQPR (SEQ ID NO:58);

[Thr$^3$(Octanoyl)]-hGhrelin:GST(CO—$C_7H_{15}$)FLSPE-HQRVQQRKESKKPPAKLQPR (SEQ ID NO:59);

[Leu$^2$,Thr$^3$ (Octanoyl)]-hGhrelin: GLT(CO—$C_7H_{15}$)FL-SPEHQRVQQRKESKKPPAKLQPR (SEQ ID NO:60);

[Lys$^3$(Octanoyl)]-hGhrelin: GSK(CO—$C_7H_5$)FLSPE-HQRVQQRKESKKPPAKLQPR (SEQ ID NO:61);

[Trp$^3$]-hGhrelin: GSWFLSPEHQRVQQRKESKKPPAK-LQPR (SEQ ID NO:62);

[Cha$^3$]-hGhrelin: GS-Cha-FLSPEHQRVQQRKESKKP-PAKLQPR (SEQ ID NO:63);

[2-$^L$NaI$^3$]-hGhrelin: GS-$^L$NaI-FLSPEHQRVQQRKESK-KPPAKLQPR (SEQ ID NO:64);

[Ser$^3$(Bzl)]-hGhrelin: GSS($CH_2$—$C_6H_5$)FLSPE-HQRVQQRKESKKPPAKLQPR (SEQ ID NO:65);

[Cys$^3$(Trityl)]-hGhrelin: GSC(C-$Ph_3$)FLSPE-HQRVQQRKESKKPPAKLQPR (SEQ ID NO:66)

[Ser$^3$ (4-Methylpentanoyl)]-hGhrelin: GSS(CO—$CH_2CH_2CH(CH_3)_2$)FLSPEHQRVQQRKESKKPPAK-LQPR (SEQ ID NO:67);

[Lys$^7$]-Ghrelin(1-7)-amide:H-Gly-Ser-Ser(CO—$C_7H_{15}$)-Phe-Leu-Ser-Lys-$NH_2$ (SEQ ID NO:68);

[N-Aminopentanoyl,Ser$^3$(Octyl),Lys$^5$]-Ghrelin(3-5)-amide: $NH_2$—$(CH_2)_4$—CO-Ser($C_8H_{17}$)-Phe-Lys-$NH_2$;

[Aib$^1$, His$^2$, Ser$^3$(Octyl), Lys$^5$]-Ghrelin(1-5)-amide: H-Aib-His-Ser($C_8H_{17}$)-Phe-Lys-$NH_2$ (SEQ ID NO:69);

[Aib$^1$,His$^2$,$^D$Ser$^3$(Octyl),$^D$Phe$^4$,Lys$^5$]-Ghrelin(1-5)-amide: H-Aib-His-$^D$Ser($C_8H_{17}$)-$^D$Phe-Lys-$NH_2$;

[Aib$^1$, His$^2$, $^D$NaI$^3$, $^D$Phe$^4$, Lys$^5$]-Ghrelin(1-5)-amide: H-Aib-His-$^D$NaI-$^D$Phe-Lys-$NH_2$;

[N-Aminopentanoyl, Ser$^3$(Octyl)]-Ghrelin(3-5)-amide: $NH_2$—$(CH_2)_4$-CO-Ser($C_8H_{17}$)-Phe-Leu-$NH_2$;

[N-Aminopentanoyl,Ser$^3$(Octyl)]-Ghrelin(3-5)-methylamide: $NH_2$—$(CH_2)_4$—CO-Ser($C_8H_{17}$)-Phe-Leu-NH—$CH_3$;

[N-Aminopentanoyl,Ser$^3$(Octyl)]-Ghrelin(3-5)-ethylamide: $NH_2$—$(CH_2)_4$—CO-Ser($C_8H_{17}$)-Phe-Leu-NH—$C_2H_5$; and

[N-Amninopentanoyl,Ser$^3$(Octyl)]-Ghrelin (3-5)-aminoethylamide: $NH_2$—$(CH_2)_4$—CO-Ser($C_8H_{17}$)-Phe-Leu-NH—$(CH_2)_2$—$NH_2$.

The aforementioned ghrelin or polypeptide derivatives of the present invention can be obtained by the known method. Examples of such methods include a method of isolation from natural raw materials, a method using recombinant DNA technique, a method of chemical synthesis, and a method of combining recombinant DNA technique and chemical synthesis. Examples of the method of isolation from natural raw materials include a method of culturing a ghrelin-producing cell of a digestive tract and isolating and purifying ghrelin. Examples of the method using recombinant DNA technique include a method of transforming a host cell which can modify a side chain of at least one amino acid residue in a polypeptide, a representative of which is a digestive tract cell, with a vector containing a ghrelin gene, culturing the resulting transformed cell, and collecting an objective polypeptide derivative from the culture. Examples of the method of chemical synthesis include a solid phase synthesis method and a liquid phase synthesis method which are conventionally used in the art. Examples of the method of combining recombinant DNA technique and chemical synthesis include a method of preparing a part of ghrelin by a chemical synthesis, preparing a remaining of ghrelin by a genetic manipulation method, and condensing both of them. More specifically, examples of a process for preparing the polypeptide derivative of the present invention include the methods described in WO 01/07475 and Japanese Patent Application No. 2003-106533.

For measuring an intracellular concentration of calcium ion, the known method can be utilized and, desirably, FLIPR (Fluorometric Imaging Plate Reader, Molecular Devices) or FLEX Station™ (Molecular Devices) utilizing a change in fluorescent intensity of Fluo-4 AM (Molecular Probe) due to a change in a concentration of calcium ion may be used.

In order to confirm GH secretion inducing activity in vitro or in vivo, the known method can be utilized. For example, in the case of in vitro, there is a method of adding a test substance to pituitary gland cells which secrete GH and have been confirmed for expression of GHS-R, and measuring GH secreted in the cell culture by radioimmunoassay using an anti-GH antibody. In addition, in the radioimmunoassay method, when an antibody against other hormone is used in place of an anti-GH antibody, a secretion amount of the hormone can be also measured. In order to confirm GH secretion inducing activity in vivo, a GH concentration in serum after injection of a test substance into a peripheral vein of animals (e.g. rat) may be measured.

A preventive or a therapeutic agent for hepatopathy of the present invention contains the aforementioned peptide derivative or a pharmacologically acceptable salt thereof. As the pharmacological acceptable salt, the same salts as those described above can be exemplified. The preventive or the therapeutic agent for hepatopathy of the present invention may contain the polypeptide derivative or a pharmacologically acceptable salt thereof, but usually, the preventive or the therapeutic agent is used by mixing an effective ingredient with the pharmacologically acceptable carrier known per se. A pharmaceutical composition consisting of the effective ingredient and, optionally, a pharmacologically acceptable carrier can take the known forms such as solid preparations including tablets, pills, powders, granules and capsules; liquid preparations such as injections and syrups; external preparations such as suppositories, eye drops, nasal drops, troches, external solutions, and aerosols. It is preferable that the preventive or the therapeutic agent for hepatopathy of the present invention have forms such as injections, nasal drops, and aerosols. Injections may take forms wherein lyophilized preparations containing the effective ingredient of the present invention and optionally a pharmacologically acceptable carrier are dissolved in a solvent upon use.

As the pharmaceutically acceptable carrier, various organic or inorganic carrier substances which are conventionally used as a formulation material are used, and they are incorporated as excipients, lubricants, binders or disintgrators in solid preparations; solutions, solubilizers, suspending agents, isotonics, buffers or soothing agents in liquid preparations. If necessary, formulation additives such as antiseptics, antioxidants, colorants and sweeteners may be used.

Preferable examples of excipients include lactose, white sugar, D-mannitol, starch, crystalline cellulose, light silicic anhydride, dextran and a derivative thereof. Preferable examples of lubricants include magnesium stearate, calcium stearate, talc and colloidal silica. Preferable examples of binders include crystalline cellulose, white sugar, D-mannitol, dextrin, hydroxypropylcellulose, hydroxypropylmethyl cellulose, polyvinylpyrrolidone, dextran and a derivative thereof. Preferable examples of disintegrators include starch, carboxymethylcellulose, potassium carboxymethylcellulose, croscarmellose sodium, and sodium carboxymethylstarch. Granules and tablets may be coated with an enteric coating agent (e.g. cellulose acetate phthalate, methacrylic acid copolymer, hydroxypropylcellulose phthalate, carboxymethylethyl cellulose, etc.). Capsules may be enteric-coated capsules, intragastric resistance-capsules, or release-controlled capsules in addition to conventional capsules. When formulated into enteric coated capsules, the aforementioned suitable excipient is added to the preventive or the therapeutic agent for hepatopathy of the present invention coated with an enteric coating agent, and the mixture is filled into conventional capsules. Alternatively, the preventive or the therapeutic agent for hepatopathy of the present invention can be filled into a capsule coated with an enteric coating agent, or a capsule formed using an enteric polymer as a base.

Preferable examples of solvents include water for injection, alcohol, propylene glycol, macrogol, sesame oil, and corn oil. Preferable examples of solubilizers include polyethylene glycol, propylene glycol, D-mannnitol, benzyl benzoate, ethanol, trisaminomethane, cholesterol, triethanolamine, sodium carbonate, and sodium citrate. Preferable examples of suspending agents include surfactants such as stearyltriethanolamine, sodium laurylsulfate, laurylaminopropionic acid, lecithin, benzalkonium chloride, benzethonium chloride, and glycerine monostearate; hydrophilic polymers such as polyvinyl alcohol, polyvinylpyrrolidone, sodium carboxymethylcellulose, methylcellulose, hydroxymethylcellulose, hydroxyethylcellulose, and hydroxypropylcellulose. Preferable examples of isotonics include sodium chloride, glycerine, and D-mannitol. Preferable examples of buffers include phosphates, acetates, carbonates, and citrates. Preferable examples of soothing agents include benzyl alcohol. Preferable examples of antiseptics include paraoxybenzoic acid esters, chlorobutanol, benzyl alcohol, phenethyl alcohol, dehydroacetic acid, and sorbic acid. Preferable examples of antioxidants include sulfites, and ascorbic acid.

When the drug of the present invention has a dosage form of suppositories, the drug of the present invention can be prepared by blending an effective ingredient of the present invention and, optionally, for example, local anesthetics, anti-histamine agents, local astringents, sulfa agents, antibiotics, wound therapeutics, surfactants, vitamins, crude drug extracts, bile acids, antiseptics, excipients, absorption promoting agents or amino acids in a lipophilic base, an aqueous base or an emulsion base.

When the drug of the present invention has a dosage form of external solutions, examples of a pharmaceutically acceptable carrier include buffers, stabilizers, antiseptics, pH adjusting agents, solvents, solbilizers, flavors, gelling agents, corrigents and refreshing agents. Examples of the solvents include glycerin, propylene glycol, ethanol, isopropanol, butylene glycol, water, sorbitol, mannitol, xylitol, ε-lucose, F-aminocaproic acid, glycine, glutamic acid salt, sodium hyaluronate, polyethylene glycols, carboxyvinyl polymers, higher alcohols such as cetanol and stearyl alcohol, medium chain fatty acid esters, fatty acid esters such as isopropyl myristate, higher fatty acids such as stearic acid, squalane, liquid paraffin, white vaseline and purified lanolin.

By using the external solutions with conventional propellants, aerosol agents can be prepared. Examples of the propellants include dimethyl ether, liquefied petroleum gas, nitrogen gas, nitrous oxide gas, carbon dioxide gas, and alternative flon gas which are normally used in an aerosol. The pressurized air may be used without using such propellants. Alternatively, a mixture of them may be used.

The polypeptide derivative of the present invention or a pharmacologically acceptable salt thereof has low toxicity, and can be used in humans or mammals except for humans (e.g. mouse, rat, rabbit, dog, cat, cow, horse, pig, monkey, etc.). Since the dose is different depending on symptom, nutrient state, age and body weight of patients, and combinatorial drug, and it can not be always said definitely, however, the dose is about 0.001 to 100 mg, preferably about 0.01 to 10 mg, more preferably about 0.1 to 10 mg per day when parenterally administered, preferably intravenously, subcutaneously or intramuscularly injected to an adult. It is desirable that this amount is administered once to a few times per day.

It is preferable that the drug of the present invention is administered to a patient intravenously, subcutaneously or intramuscularly and, in the case of home care, oral administration, nasal administration, lung administration, and suppository administration are desirable. The administration period is preferably about 4 to 24 weeks, more preferably about 4 to 12 weeks.

The preventive or the therapeutic agent for hepatopathy in accordance with the present invention is particularly effective in hepatitis, liver cirrhosis or hepatic insufficiency. Examples of the hepatitis include viral hepatitis, alcoholic hepatitis, drug hepatitis and autoimmune hepatitis.

The preventive or the therapeutic agent for hepatopathy in accordance with the present invention can be also used as an agent for promoting hepatic regeneration and hepatic function recovery after liver operation utilizing hepatocyte proliferation promoting activity of polypeptide derivatives or pharmacologically acceptable salts thereof. Specifically, liver operation includes hepatectomy, and the like.

EXAMPLES

The present invention will be explained in detail by way of Examples, but it goes without saying that the present invention is not limited to them.

Example 1

Ghrelin administration experiment using dimethylnitrosoamine (DMN)-induced hepatic fibrosis/liver cirrhosis model (Estimation of survival rate).

A hepatic fibrosis/liver cirrhosis rat model to be induced by DMN was prepared, rat ghrelin was subcutaneously injected, and the effect on hepatopathy was investigated. A time flow of the present Example is shown in FIG. 1.

(1) Preparation of DMN-Induced Hepatic Fibrosis/Liver Cirrhosis Model

Upon use, a dilution in which DMN (manufactured by Wako Pure Chemical Industries, Ltd.) was diluted with a physiological saline solution (manufactured by Otsuka Pharmaceutical Co., Ltd., physiological saline solution described in the Japanese Pharmacopoeia) to 1% concentration (v/v) was prepared, and this was intraperitoneafly administered to male rats (4 weeks old) so that DMN became 1 mL/kg. Administration was performed once a day, for consecutive three days in one week, and administration was repeated for 6 weeks, and the first time administration date was regarded as day 1.

(2) Preparation of Dosing Solution

Rat ghrelin (purchased from Peptide Institute Inc., Japan) was added to 5 weight % mannitol as a solvent to a concentration of 1 mg/mL, this was dispensed every necessary amount per one time, and freezing-stored at about −80° C. until its use. Upon use, this was thawed, and diluted with a physiological saline solution to a concentration of 30 μg/mL and 3 μg/mL to obtain a dosing solution.

(3) Ghrelin Administration

Each 1 mL/kg of dosing solution containing 3 μg/mL ghrelin or 30 μg/mL of ghrelin prepared in (2) was subcutaneously administered to the DMN-treated rat obtained in (1) at the back. In addition, as a control group, 1 mL/kg of a physiological saline not containing ghrelin was subcutaneously administered to the DMN-treated rat obtained in (1) at the back. The administration was performed once a day every day from DMN first time administration date (day 1), over 8 weeks.

(4) Result

Figure 2:
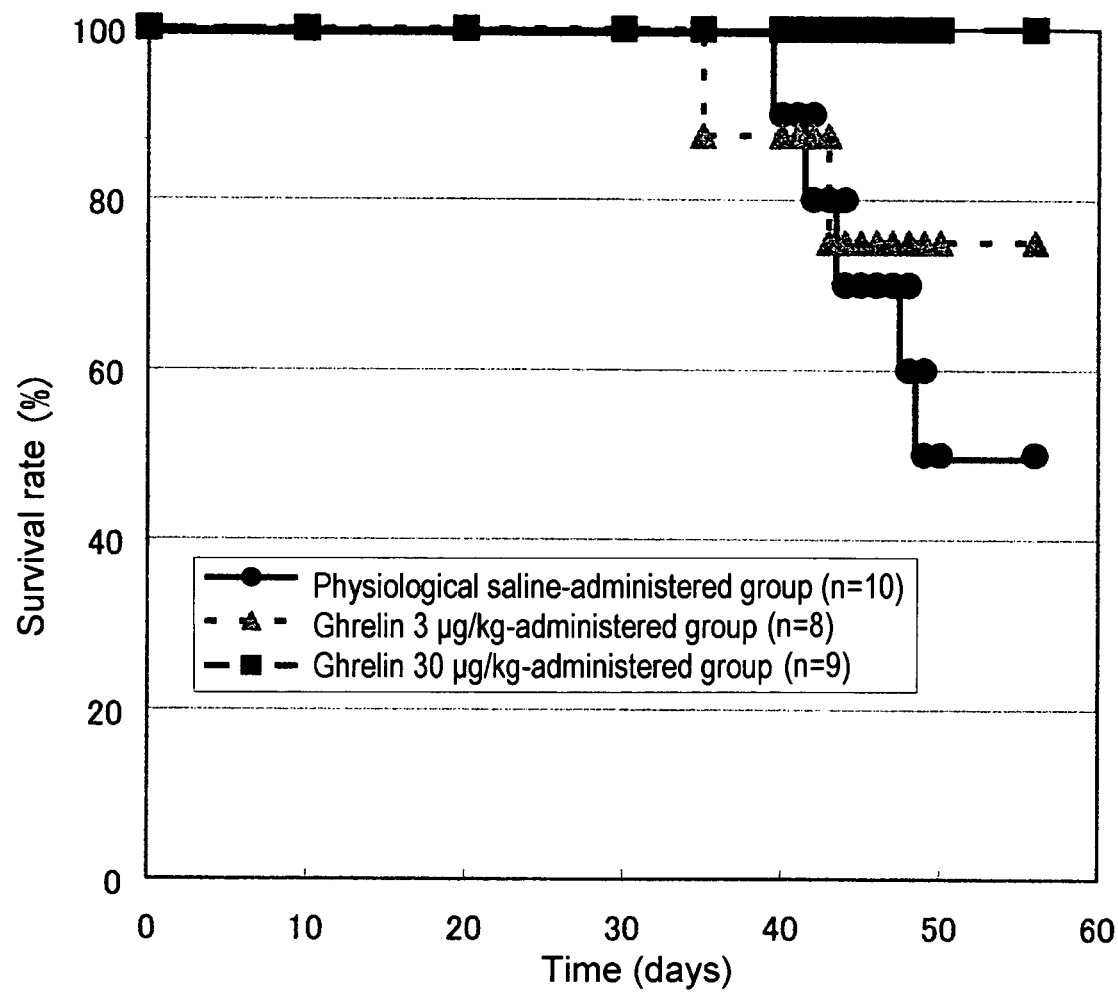
FIG. 2 shows a survival curve of a physiological saline-administered group, a ghrelin 3 µg/kg-administered group and a ghrelin 30 µg/kg-administered group in Example 1.

Survival curves of a physiological saline-administered group, a ghreline 3 μg/kg-administered group and a 30 μg/kg-administered group are shown in FIG. 2. In the physiological saline-administered group, death case began to appear 40 days after the initiation of treatment, and a half died at 56 days. To the contrary, in rats of the ghrelin 3 μg/kg-administered group, 75% survived at 56 days and, in the ghrelin 30 μg/kg-administered group, all cases survived. From the above results, it was proven that ghrelin has the effect of dramatically reducing a mortality in a DMN-induced hepatic fibrosis/liver cirrhosis model.

Example 2

Ghrelin administration experiment using DMN-induced hepatic fibrosis/liver cirrhosis model (Estimation of various parameters)

According to the same manner as that of Example 1 except that administration days were changed from 8 weeks to 35 days, an experiment was performed, and the effect of rat ghrelin on hepatopathy was estimated from a viewpoint of organ weight, hematology and serum biochemistry. A DMN-untreated group (normal rat) was used as a control group.

(1) Organ Weight

Table 1 shows organ weights, and ascites appearance frequency before and after subcutaneous injection of a physiological saline or ghrelin to a DMN-induced hepatic fibrosis rat together with data of normal rats. Δ organ weight (g) in Table was calculated by the following equation; Δ organ weight (g)=organ weight 35 days after administration (g)−organ weight before administration (g), and each value in Table shows mean±S.E.

Liver weight of the physiological saline-administered group and the ghrelin 3 μg/kg-administered group was reduced as compared with a normal rat, while there was a tendency that reduction in the liver weight was suppressed in the ghrelin 30 μg/kg-administered group. Spleen weight was increased to more than 2-fold in the physiological saline-administered group and the ghrelin 3 μg/kg-administered group as compared with normal rats, while increase was slightly suppressed in the ghrelin 30 μg/kg-administered group. Ascites appearance was observed in nearly half of rats in the physiological saline-administered group, while ascites did not appear in the ghrelin 30 μg/kg-administered group.

TABLE 1

| Group | Number | Δ liver weight (g) | Δ spleen weight (g) | Ascites |
|---|---|---|---|---|
| Controll group (normal rat) DMN treatment | 5 | 15.9 ± 0.7 | 1.01 ± 0.03 | 0/5 |
| Physiological saline-administered group | 7 | 13.6 ± 0.6 * | 2.32 ± 0.16 ** | 3/7 |
| Ghrelin 3 μg/kg - administered group | 7 | 13.6 ± 0.7 | 2.20 ± 0.08 | 2/7 |
| Ghrelin 30 μg/kg - administered group | 7 | 14.3 ± 0.6 | 1.83 ± 0.12 *** | 0/7 |

In Table,
* indicates that there is a significant difference of $p < 0.05$ relative to the control group.
** indicates that there is a significant difference of $p < 0.001$ relative to the control group.
*** indicates that there is a significant difference of $p < 0.05$ relative to the physiological saline-administered group.

(2) Hematology

Table 2 shows hematology data before and after subcutaneous injection of a physiological saline or ghrelin to a DMN-induced hepatic fibrosis rat together with data of normal rats.

As compared with normal rats, in the physiological saline-administered group, there was a tendency that the number of leukocytes was increased by DMN treatment, and a tendency that the number of erythrocytes was decreased, and the number of platelets was decreased was observed. However, by ghrelin 30 μg/kg administration, the number of platelets was recovered. In addition, a tendency that the number of other hemocytes was returned to a normal level was shown.

TABLE 2

| Group | Number | Leukocyte ($\times 10^3$/μL) | Erythrocyte ($\times 10^6$/μL) | Platelet ($\times 10^4$/μL) |
|---|---|---|---|---|
| Control group (normal rat) DMN treatment | 5 | 3.9 ± 0.4 | 7.5 ± 0.2 | 75.6 ± 7.9 |
| Physiological saline-administered group | 7 | 7.9 ± 1.6 | 6.5 ± 0.2 * | 50.9 ± 8.4 |
| Ghrelin 3 μg/kg - administered group | 7 | 7.3 ± 0.6 | 6.4 ± 0.2 | 52.3 ± 6.2 |
| Ghrelin 30 μg/kg - administered group | 7 | 6.6 ± 1.2 | 6.8 ± 0.3 | 89.6 ± 5.5 ** |

In Table,
* indicates that there is a significant difference of $p < 0.005$ relative to the control group.
** indicates that there is a significant difference of $p < 0.005$ relative to the physiological saline-administered group.

(3) Serum Biochemistry

Table 3 shows coagulation fibrinolysis systems data before and after subcutaneous injection of a physiological saline or ghrelin to a DMN-induced hepatic fibrosis rat together with data of normal rats.

As compared with normal rats, in the physiological saline-administered group, it was observed that serum fibrinogen was tended to be decreased and hepaplastin time was tended to be prolonged. However, by ghrelin administration, a tendency that fibrinogen was recovered to normalization, and hepaplastin time was also tended to be normalized.

TABLE 3

| Group | Number | Fibrinogen (g/L) | Hepaplastin time (sec) |
|---|---|---|---|
| Control group (normal rat) DMN treatment | 5 | 247.5 ± 11.4 | 67.8 ± 3.1 |
| Physiological saline-administered group | 7 | 151.2 ± 16.3* | 100.2 ± 14.2 |
| Ghrelin 3 μg/kg-administered group | 7 | 166.3 ± 9.5 | 86.2 ± 11.8 |
| Ghrelin 30 μg/kg-administered group | 7 | 207.3 ± 16.3 ** | 77.8 ± 3.2 |

In Table,
* indicates that there is a significant difference of $p < 0.005$ relative to the control group.
** indicates that there is a significant difference of $p < 0.005$ relative to the physiological saline-administered group.

Example 3

Rat hepatocyte proliferation promoting activity by repeated administration of ghrelin for one week 10 μg/kg of ghrelin was repeatedly administered intravenously to Wistar male rats two times a day for 7 days and, on the next day from administration completion, liver was isolated and fixed. Then, ki-67 protein as a peptide which is expressed at cell growth phase was immunostained.

For quantatively assessing hepatocyte proliferation activity by ghrelin, eight places of the liver section of one case of the physiological saline-administered group and one case of the ghrelin-administered group were arbitrarily selected, and among about 200 hepatocytes in a visual field, the number of ki-67 positive cells was counted under a microscope.

Figure 3:
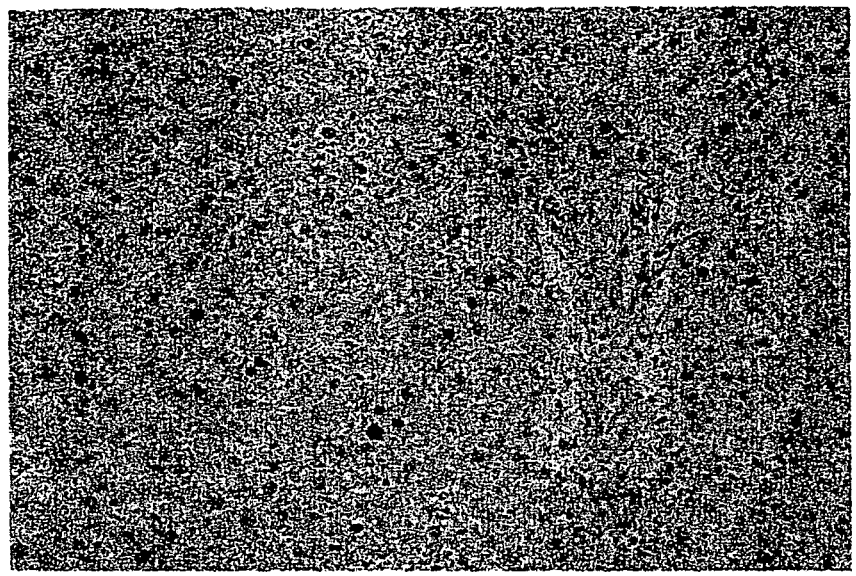
FIG. 3 shows a light microscope photograph of rat hepatocytes immunostained with ki-67 protein. A is a photograph of a physiological saline-administered group, and B is a photograph of a ghrelin-administered group.
Figure 3:
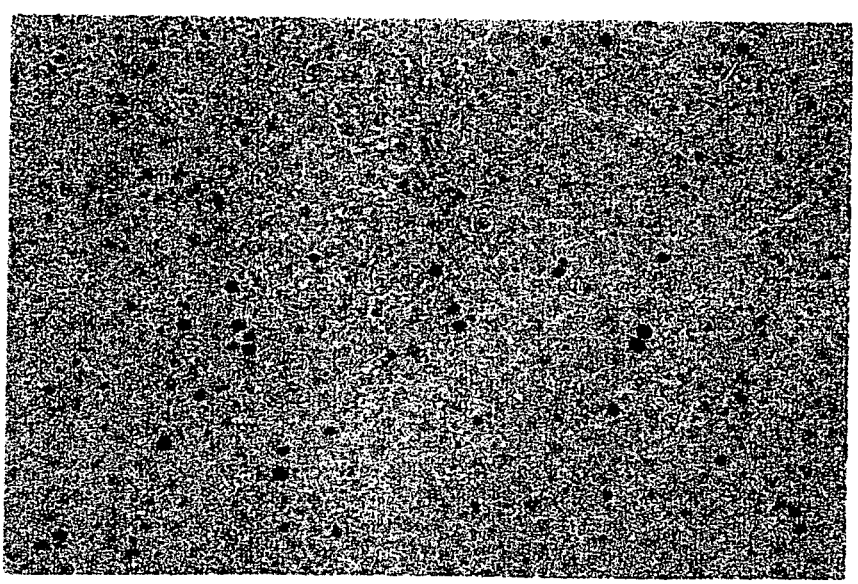

As shown in FIG. 3, when ki-67 positive cells were counted under a light microscope, and compared with the physiological saline-administered group, cells at the growth phase were about 2 to 10-fold increased in the ghrelin-administered group as compared with the physiological saline-administered group.

In addition, as shown in the following Table, in the physiological saline-administered group, the number of ki-67 positive cells was 2.5±1.2 among 228±27 of observed hepatocytes, and the ratio was 1.07±0.40%. To the contrary, in the ghrelin-administered group, among 231±27 of hepatocytes, 20.9±6.1 ($p<0.0001$) was ki-67 positive, and the ratio was 9.28±3.26%.

TABLE 4

| | Physiological saline-administered group | Ghrelin-administered group |
|---|---|---|
| Number of observed total cells | 228 ± 27 | 231 ± 27 |
| Number of ki-67 positive cells | 2.5 ± 1.2 | 20.9 ± 6.1 |

TABLE 4-continued

|  | Physiological saline-administered group | Ghrelin-administered group |
|---|---|---|
| Positive ratio | 1.07 ± 0.40 | 9.28 ± 3.26 |
| P value (*) | — | p < 0.0001 |

(*) p value calculated based on t-test of ghrelin-administered group relative to physiological saline-administered group.

Example 4

Liver Weight after Hepatectomy

Seventy % of liver was excised under anesthesia in Wistar male rats, and 30 μg/kg of ghrelin or a physiological saline was subcutaneously injected two times a day for 3 days under 40% restricted diet. Four days after, rat liver was isolated, and the liver weight was measured.

In the rat under 40% restricted diet, as compared with a group of subcutaneous injection of a physiological saline after hepatectomy, the liver weight was increased in a group of subcutaneous injection of ghrelin (Table 5).

TABLE 5

| Administration | Liver weight | Number |
|---|---|---|
| Physiological saline-administered group | 2.243 ± 0.119 | 7 |
| Ghrelin 30 μg/kg- administered group | 2.464 ± 0.133* | 5 |

In Table,
* indicates significance at a level of $p < 0.05$ relative to the physiological saline-administered group.

In the morbid state at hepatopathy such as hepatitis, liver cirrhosis and liver cancer after hepatectomy, digestive tract disorder is seen, the nutrient state is exacerbated in many cases, food intake is insufficient, and recovery is insufficient in many cases (Internal Drug Book 3, supervised by Yamamura and Yoshitoshi, Nakayama-Shoten Co., Ltd., p. 1095-1250 (1987)). In study under restricted intake, recovering effect of ghrelin under such severe condition was studied.

After hepatectomy in liver cirrhosis or liver cancer, or in liver transplantation or liver regeneration drug, it is shown that ghrelin promotes hepatocyte regeneration, and is useful for prevention of disorder or early curing.

Example 6

Organ Blood Flow

Ghrelin 30 μg/kg or a physiological saline was subcutaneously injected to Wistar male rats under anesthesia, 1.5 million of microspheres (diameter 15.5 μm, Triron Technology Inc.) were immediately administered intravenously, an organ was isolated one minute later, an amount of microspheres in an organ was measured, and an organ blood flow per time was measured (Sharon L. et al., Circulation, 78, p. 428-434 (1988); Kawai J. et al., Hypertens. Res., 25, p. 441-446 (2002)).

As compared with the physiological saline-administered group (control), in the ghrelin-administered group, an amount of organ blood flow in the liver, spleen and stomach was increased (p<0.05), and a tendency of blood flow increase was shown in jejunum (Table 6).

TABLE 6

| Group | Hepatic blood flow (mL/min/kg) | Spleen blood flow (mL/min/kg) | Stomach blood flow (mL/min/kg) |
|---|---|---|---|
| Physiological saline-administered group | 0.554 ± 0.185 | 0.627 ± 0.289 | 0.426 ± 0.271 |
| Ghrelin 30 μg/kg-administered group | 1.049 ± 0.414 ** | 1.099 ± 0.264 * | 1.064 ± 0.486 ** |
| Ghrelin 30 μg/kg + atropine-administered group | 0.650 ± 0.176 | 0.829 ± 0.432 | 0.584 ± 0.218 |

In the Table,
each value indicates mean ± standard deviation (6 rats per group).
In the Table,
* indicates that there is a significant difference at a level of $p < 0.05$ relative to the physiological saline-administered group, and
** indicates that there is a significant difference at a level of $p < 0.01$ relative to the physiological saline-administered group.

It is known that, in the case of disorder such as liver cirrhosis, an amount of hepatic blood flow is reduced, and a spleen amount is increased, and it is suggested that this leads to disorder such as deterioration of hepatic function and platelet reduction (Internal Drug Book 3, supervised by Yamamura and Yoshitoshi, Nakayama syoten, p. 1095-1250 (1987)).

Since ghrelin administration increased blood flow in these organs, it has been shown that ghrelin is useful for suppressing organ damage seen at hepatopathy. That is, it is known that, in liver cirrhosis, due to proliferated connective tissue and regenerated node, stenosis and occlusion of hepatic vein branch occur, increase in portal pressure and hepatic congestion are induced, leakage of hepatic lymph occurs, and this becomes a cause for generating ascites (Internal Drug Book 3, supervised by Yamamura and yoshitoshi Nakayama-Shoten Co., Ltd., p. 1095-1250 (1987)). Ghrelin which can increase hepatic blood flow can be expected as a drug which can prevent or treat the morbid state such as varix and splenoma which may be generated based on these symptoms.

Example 7

Amount of expression of hepatocyte proliferation marker (PCNA) and HGF

Amounts of expression of a PCNA mRNA and a HGF mRNA in the liver after subcutaneous injection of a physiological saline and ghrelin to DMN-induced hepatic fibrosis rats were measured by the real time RT-PCR method. Amounts of expression of a PCNA mRNA and a HGF mRNA are shown in Table 7.

TABLE 7

| Group | PCNA mRNA | HGF mRNA |
| --- | --- | --- |
| Physiological saline-administered group | 1.597 ± 0.269 | 1.317 ± 0.352 |
| Ghrelin 30 µg/kg-administered group | 2.083 ± 0.533 | 2.025 ± 0.595 |

In a group of ghrelin administration to a DMN-induced hepatic fibrosis rat, expression of a HGF mRNA was increased ($p<0.05$), and expression of a PCNA mRNA was tended to be increased as compared with the physiological saline-administered group. These results show that, in the morbid state such as hepatic fibrosis, ghrelin exerts on a regeneration or function recovery of hepatocytes via increase in HGF expression, and is useful for maintaining hepatic function.

In addition, these results show that a derivative of a polypeptide used in the present invention having an activity of increasing an intracellular calcium concentration via GHS-R, including, for example, human ghrelin, is useful for hepatic function disorder based on hepatic diseases such as liver cirrhosis and hepatic regeneration and hepatic function recovery after hepatectomy, as in the aforementioned Examples.

INDUSTRIAL APPLICABILITY

A polypeptide derivative which is an effective ingredient in the present invention can prevent hepatic function disorder which occurs in hepatic diseases such as hepatitis, liver cirrhosis and hepatic insufficiency, and is useful for treating these diseases and preventing progression of these diseases.

In addition, a polypeptide derivative which is an effective-ingredient in the present invention has hepatocyte proliferation promoting activity, and is also useful as an agent for promoting hepatic regeneration/hepatic function recovery after liver operation, particularly, hepatectomy.

Further, since a polypeptide derivative shows little side effects in animal experiments using rats, the derivative has also advantage that it can be safely administered to mammals including humans.

The invention claimed is:

1. A method for promoting hepatic regeneration and/or hepatic function recovery after hepatectomy, the method comprising administering to a mammal in need thereof a polypeptide derivative capable of binding to growth hormone secretagogue receptor and elevating intracellular calcium ion concentration, or a salt thereof, the derivative consisting of an amino acid sequence selected from SEQ ID NOS: 1 to 16, 19 to 22, or combinations thereof, wherein the second or third amino acid residue from the amino-terminus of the amino acid sequence comprises a serine or a group represented by the formula (2),

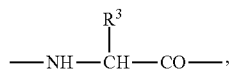
(2)

wherein $R^3$ is $-T^2-P^2-Q^2$, $T^2$ is methylene, $P^2$ is $-CO-O$, and $Q^2$ is an optionally substituted $C_{1-20}$ alkyl group.

2. The method of claim 1, wherein said polypeptide derivative further comprises a basic amino acid bound to the carboxyl-terminus.

3. The method of claim 1, wherein the carboxyl group of the polypeptide derivative at the carboxyl-terminus forms a salt, ester or amide.

4. The method of claim 1, wherein the dose of the polypeptide derivative per day is about 0.001 to about 100 mg.

5. The method of claim 1, wherein $Q^2$ is a $C_{1-20}$ alkyl group.

6. The method of claim 5, wherein $Q^2$ is a $C_7$ alkyl group.

7. The method of claim 1, wherein said mammal is a human.

8. The method of claim 1, wherein the amino acid sequence is any one of SEQ ID NOS: 1 to 10 or SEQ ID NO. 22.

9. The method of claim 1, wherein the amino acid sequence is SEQ ID NO: 1 or 2, and wherein a side chain hydroxyl group of the third serine residue from the amino-terminus is acylated with acetic acid, butyric acid, valeric acid, octanoic acid or decanoic acid.

10. The method of claim 9, wherein the amino acid sequence is SEQ ID NO: 1, and wherein the side chain hydroxyl group of the third serine residue from the amino-terminus is acylated with octanoic acid.

* * * * *